United States Patent
Gaynes et al.

(10) Patent No.: US 12,201,499 B2
(45) Date of Patent: Jan. 21, 2025

(54) MYRINGOTOMY TOOL WITH MULTIPLE TOOL HEADS

(71) Applicant: GYRUS ACMI, INC., Westborough, MA (US)

(72) Inventors: Steve Gaynes, Mchenry, IL (US); Michael O'Connor, Gurnee, IL (US); Michael DeRossi, Lindenhurst, IL (US); Gilberto Cavada, Wauconda, IL (US); John Morici, Wauconda, IL (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 137 days.

(21) Appl. No.: 18/149,496

(22) Filed: Jan. 3, 2023

(65) Prior Publication Data
US 2023/0144549 A1   May 11, 2023

Related U.S. Application Data

(63) Continuation of application No. 16/822,290, filed on Mar. 18, 2020, now Pat. No. 11,571,338, which is a
(Continued)

(51) Int. Cl.
*A61F 11/20* (2022.01)
*A61B 1/00* (2006.01)
(Continued)

(52) U.S. Cl.
CPC .......... *A61F 11/20* (2022.01); *A61B 1/00066* (2013.01); *A61B 1/00133* (2013.01);
(Continued)

(58) Field of Classification Search
CPC ............ A61B 1/00052; A61B 1/00066; A61B 1/00133; A61B 1/015; A61B 1/018;
(Continued)

(56) References Cited

U.S. PATENT DOCUMENTS

| 3,913,584 A | 10/1975 | Walchle et al. |
| 6,106,520 A | 8/2000 | Laufer et al. |

(Continued)

OTHER PUBLICATIONS

"U.S. Appl. No. 15/464,460, 312 Amendment filed Dec. 19, 2019", 5 pgs.
(Continued)

*Primary Examiner* — Mohamed G Gabr
(74) *Attorney, Agent, or Firm* — Schwegman Lundberg & Woessner, P.A.

(57) ABSTRACT

A myringotomy device includes a housing; an elongated tube extending from the housing; and a retractable cutting tool extendable through the elongated tube, the cutting tool comprising a blade. The cutting tool is configured such that when advanced, the blade of the cutting tool extends beyond a distal end of the elongated tube. The cutting tool is also configured such that when retracted, the blade is retracted into the elongated tube and a fluid conduit is created from the distal end of the elongated tube to the housing.

18 Claims, 27 Drawing Sheets

Related U.S. Application Data continuation of application No. 15/464,460, filed on Mar. 21, 2017, now Pat. No. 10,639,200.

(60) Provisional application No. 62/329,223, filed on Apr. 29, 2016, provisional application No. 62/311,429, filed on Mar. 22, 2016.

(51) Int. Cl.

| | | |
|---|---|---|
| *A61B 1/015* | (2006.01) | |
| *A61B 1/018* | (2006.01) | |
| *A61B 1/227* | (2006.01) | |
| *A61B 17/00* | (2006.01) | |
| *A61B 17/22* | (2006.01) | |
| *A61B 17/32* | (2006.01) | |
| *A61B 17/34* | (2006.01) | |
| *A61B 90/00* | (2016.01) | |
| *A61B 90/30* | (2016.01) | |

(52) U.S. Cl.
CPC .............. *A61B 1/015* (2013.01); *A61B 1/018* (2013.01); *A61B 1/227* (2013.01); *A61B 17/32002* (2013.01); *A61B 17/3415* (2013.01); *A61B 17/3468* (2013.01); *A61F 11/202* (2022.01); *A61B 1/00052* (2013.01); *A61B 17/00234* (2013.01); *A61B 2017/00353* (2013.01); *A61B 2017/0038* (2013.01); *A61B 2017/00787* (2013.01); *A61B 2017/22074* (2013.01); *A61B 2017/320032* (2013.01); *A61B 90/30* (2016.02); *A61B 2090/309* (2016.02); *A61B 90/361* (2016.02); *A61B 90/37* (2016.02); *A61B 2217/005* (2013.01); *A61B 2217/007* (2013.01)

(58) Field of Classification Search
CPC .............. A61B 1/227; A61B 17/00234; A61B 17/32002; A61B 17/3415; A61B 17/3468; A61B 2017/00353; A61B 2017/0038; A61B 2017/00738; A61B 2017/00787; A61B 2017/22074; A61B 2017/320032; A61B 2090/309; A61B 2217/005; A61B 2217/007; A61B 90/30; A61B 90/361; A61B 90/37; A61F 11/20; A61F 11/202
See application file for complete search history.

(56) References Cited

U.S. PATENT DOCUMENTS

| | | | |
|---|---|---|---|
| 6,565,527 | B1 | 5/2003 | Jonkman et al. |
| 8,814,847 | B2 | 8/2014 | Hoffman et al. |
| 8,945,142 | B2 | 2/2015 | Schaeffer et al. |
| 9,174,032 | B2 | 11/2015 | Zhou et al. |
| 10,639,200 | B2 | 5/2020 | Gaynes et al. |
| 11,571,338 | B2 | 2/2023 | Gaynes et al. |
| 2004/0138562 | A1 | 7/2004 | Makower et al. |
| 2008/0051804 | A1* | 2/2008 | Cottler .................. A61F 11/202 606/109 |
| 2011/0201996 | A1 | 8/2011 | Melder |
| 2012/0179187 | A1 | 7/2012 | Loushin et al. |
| 2013/0023914 | A1 | 1/2013 | Truong et al. |
| 2015/0157415 | A1 | 6/2015 | Peyman |
| 2015/0290040 | A1* | 10/2015 | Vaughan ................ A61F 11/202 606/109 |
| 2017/0296388 | A1 | 10/2017 | Gaynes et al. |
| 2020/0214893 | A1 | 7/2020 | Gaynes et al. |

OTHER PUBLICATIONS

"U.S. Appl. No. 15/464,460, Non Final Office Action mailed Jun. 14, 2019", 11 pgs.
"U.S. Appl. No. 15/464,460, Notice of Allowance mailed Dec. 18, 2019", 13 pgs.
"U.S. Appl. No. 15/464,460, Preliminary Amendment filed May 18, 2017", 5 pgs.
"U.S. Appl. No. 15/464,460, PTO Response to Rule 312 Communication mailed Jan. 24, 2020", 2 pgs.
"U.S. Appl. No. 15/464,460, Response filed Feb. 27, 2019 to Restriction Requirement mailed Jan. 31, 2019", 2 pgs.
"U.S. Appl. No. 15/464,460, Response filed Aug. 23, 2019 to Non Final Office Action mailed Jun. 14, 2019", 19 pgs.
"U.S. Appl. No. 15/464,460, Restriction Requirement mailed Jan. 31, 2019", 9 pgs.
"U.S. Appl. No. 16/822,290, Final Office Action mailed Jun. 24, 2022", 9 pgs.
"U.S. Appl. No. 16/822,290, Non Final Office Action mailed Dec. 21, 2021", 10 pgs.
"U.S. Appl. No. 16/822,290, Notice of Allowance mailed Oct. 6, 2022", 8 pgs.
"U.S. Appl. No. 16/822,290, Response filed Mar. 21, 2022 to Non Final Office Action mailed Dec. 21, 2021", 12 pgs.
"U.S. Appl. No. 16/822,290, Response filed Sep. 26, 2022 to Final Office Action mailed Jun. 24, 2022", 10 pgs.

* cited by examiner

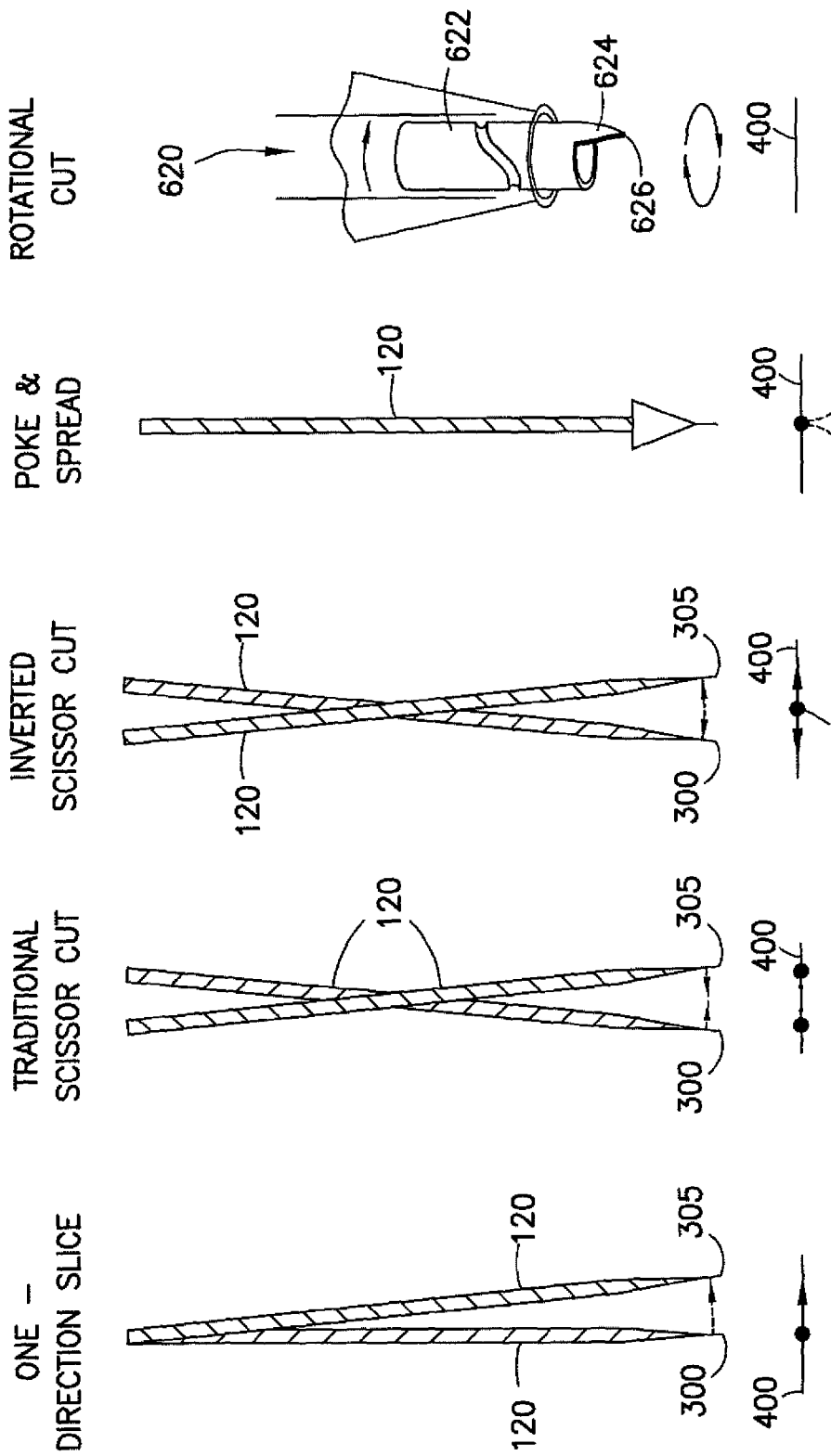

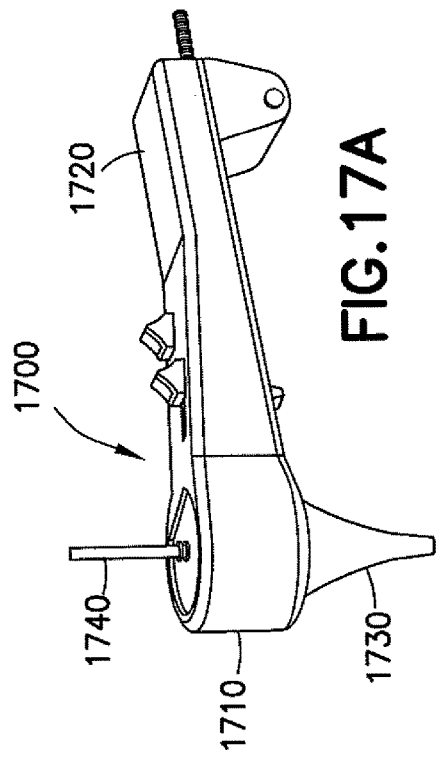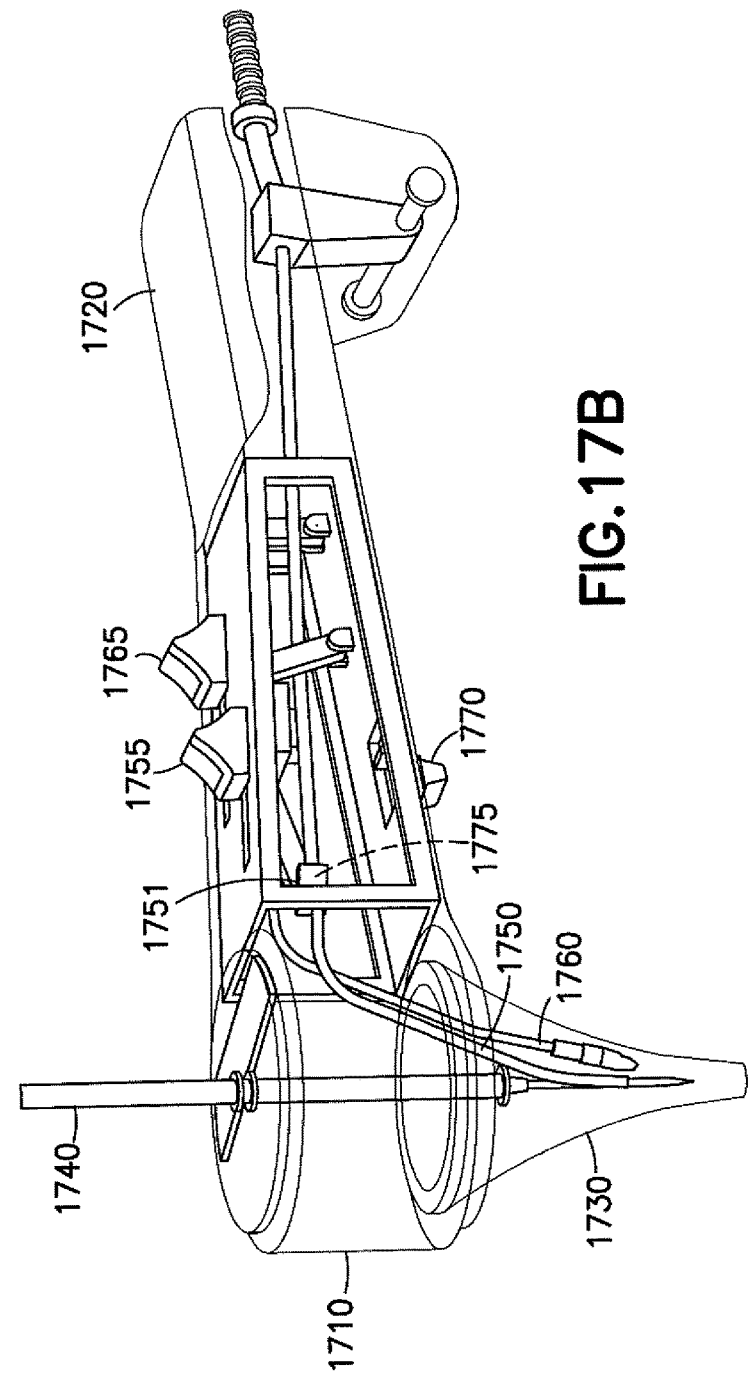

MYRINGOTOMY TOOL WITH MULTIPLE TOOL HEADS

CROSS REFERENCE

This patent application is a continuation of U.S. patent application Ser. No. 16/822,290, filed on Mar. 18, 2020, which is a continuation of U.S. patent application Ser. No. 15/464,460, filed on Mar. 21, 2017 and now issued as U.S. Pat. No. 10,639,200, which claims priority to Provisional Patent Application No. 62/311,429, filed on Mar. 22, 2016, and Provisional Patent Application No. 62/329,223, filed on Apr. 29, 2016, the disclosures of which are incorporated by reference herein in their entireties.

BACKGROUND

Field of the Invention

The exemplary and non-limiting embodiments described herein relate to medical devices and, more specifically, to medical devices for myringotomy procedures.

Brief Description of Prior Developments

A myringotomy is a surgical procedure in which an incision is made in a tympanic membrane (eardrum) of a patient. The incision is typically made to relieve pressure caused by excessive fluid collection in the middle ear, generally defined by the tympanic cavity, which is the space between the eardrum and the oval window of the inner ear. In a myringotomy, a tympanostomy tube (ear tube), which is a small conduit through which fluid may pass, is inserted through the incision in the eardrum to aerate the tympanic cavity and/or to drain fluid therefrom. A patient may undergo a myringotomy procedure due to an obstructed Eustachian tube (which extends from the tympanic cavity to the nasal cavity) or one that otherwise inadequately drains or vents the tympanic cavity. Obstructions or inadequately draining or venting tympanic cavities may result from infections caused by a virus or bacteria or from an irritant or allergy in the nasal cavity.

A myringotomy procedure generally involves various tools. For example, the incision in the eardrum is generally made by a cutting tool. Also, the ear tube is generally inserted into the incision using a delivery tool. Furthermore, the myringotomy procedure may additionally involve a suction tool, an irrigation tool, a camera or other viewing tool, and/or an illumination tool.

SUMMARY

In accordance with one aspect of the invention, a myringotomy device comprises a housing; an elongated tube extending from the housing; and a retractable cutting tool extendable through the elongated tube, the cutting tool comprising a blade. The cutting tool is configured such that when advanced, the blade of the cutting tool extends beyond a distal end of the elongated tube. The cutting tool is also configured such that when retracted, the blade is retracted into the elongated tube and a fluid conduit is created from the distal end of the elongated tube to the housing.

In accordance with another aspect of the invention, a myringotomy device comprises a housing; an elongated shaft extending from the housing; an ear tube held on the outside of the elongated shaft at a chamber position that is a distance from a distal end of the elongated tube; and a movable tube configured to push or carry the ear tube over the elongated shaft to the distal end of the elongated shaft.

In accordance with another aspect of the invention, a myringotomy tool may comprise a housing and an extended shaft having a distal end with at least one tool located at the distal end. The extended shaft has a bend between the proximal end and the distal end of the shaft such that the straight length of shaft distal to the bend can be viewed on axis.

In accordance with another aspect of the invention, a myringotomy tool comprises a handpiece; an elongated tube extending from the handpiece; a blade shaft extending down the elongated tube and being extendable beyond a distal end of the elongated tube; and a knob on the handpiece, the knob being cooperably coupled to the blade shaft. The knob is configured to rotate the blade shaft when turned.

In accordance with another aspect of the invention, a myringotomy device may comprise a housing; a speculum coupled to the housing; two or more tools located in the housing, each of the two or more tools being coupled to a distal end of a tool carrier in the housing; and a linkage for delivering each of the two or more tools serially through the speculum.

In accordance with another aspect of the invention, a method of performing a myringotomy procedure comprises causing a retractable cutting tool to extend through a hollow elongated tube depending from a housing, the cutting tool comprising a blade; making an incision in an ear drum using the retractable cutting tool; retracting the retractable cutting tool; and causing an ear tube to be delivered from the elongated tube to the incision.

In accordance with another aspect of the invention, a method of assembling a myringotomy tool comprises providing a housing; extending an elongated shaft from the housing; providing at least a cutting tool and an ear tube delivery tool in the housing; and causing the cutting tool and the ear tube delivery tool to be serially deliverable from a distal end of the elongated shaft.

BRIEF DESCRIPTION OF THE DRAWINGS

The foregoing aspects and other features of the invention are explained in the following description, taken in connection with the accompanying drawings, wherein:

FIGS. 6A-6E are schematic representations of various cutting operations using a myringotomy device;

FIGS. 17A-17F are representations of another example embodiment of a myringotomy device having a pivot center manifold;

DETAILED DESCRIPTION

Figure 1:
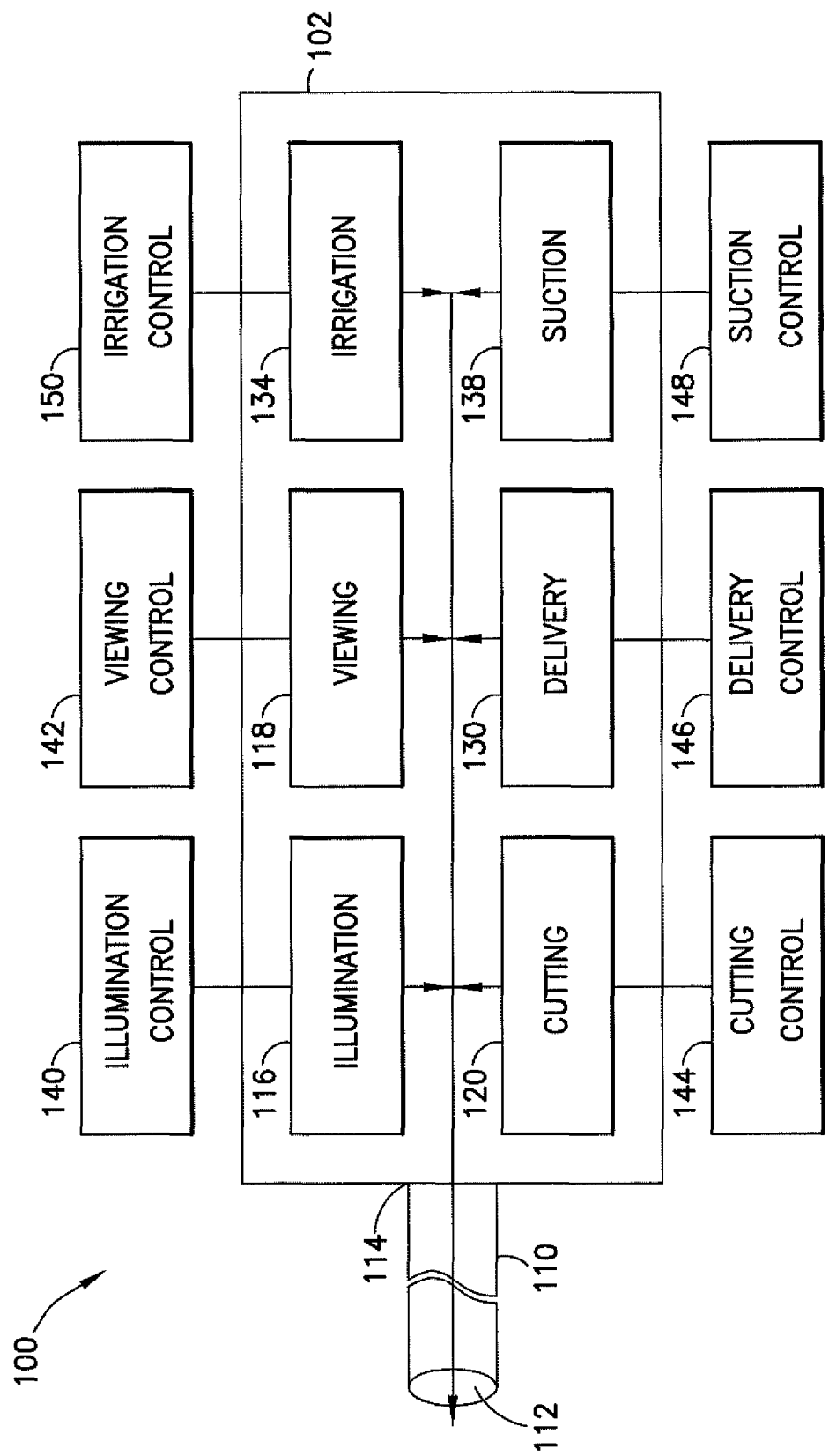
FIG. 1 is a schematic representation of one example embodiment of a device for use in a myringotomy procedure.

Referring to FIG. 1, one exemplary embodiment of a myringotomy device is designated generally by the reference number 100 and is hereinafter referred to as "device 100." Although the features will be described with reference to the example embodiments shown in the drawings, it should be understood that features can be embodied in many alternate forms. In addition, any suitable size, shape, or type of elements or materials may be used.

Device 100 may be used in a myringotomy having a plurality of steps. Such steps include, but are not limited to, illuminating, viewing, cutting, delivering an ear tube, and/or suctioning. Each step may utilize or benefit from a specific tool.

Device 100 comprises a handpiece or handle or housing 102, a plurality of tool heads or tools located in the housing 102, the tools being configured to carry out the steps of a myringotomy, and a distally extending tube 110 having a distal end 112 through which the tools may be delivered and a proximal end 114 through which the tools may be controlled when the tube 110 is inserted by a surgeon into a patient's ear canal. The tools may be movable within the housing 102 on a carousel or around an axis or the like for delivery through the tube 110. The tube 110 may be a single tubular member that is flexible and adaptable to a multitude of functions. The use of a single tubular member reduces the profile of the tools at the distal end of the tube 110. The length of the tube 110 may be such a length so as to allow the housing 102 to be positioned out of the line of sight of the surgeon. A combination of the flexibility and the reduced tool profile further aids in the preservation of a line of sight of the surgeon.

Tools that may be incorporated into the device 100 include, but are not limited to, illumination tools 116 (e.g., lights), viewing tools 118 (e.g., scopes), cutting tools 120 (e.g., knives or other bladed tools), delivery tools 130 (e.g., tools that can place and/or selectively release objects), irrigation tools 134, suction tools 138 (e.g., vacuum systems), and the like. Each tool may have an associated control. For example, the illumination tools 116 may have an illumination control 140, the viewing tools 118 may have a viewing control 142, the cutting tools 120 may have a cutting control 144, the delivery tools 130 may have a delivery control 146, the irrigation tools 134 may have an irrigation control 150, and the suction tools 138 may have a suction control 148.

Also included inside the housing 102 may be a cutting tool retraction mechanism, which may be a magnetic mechanism. In other embodiments, the cutting tool retraction mechanism may cause retraction of the cutting tool 120 using suction. Further included inside the housing 102 may be a shuttle mechanism for use with the delivery tool 130, the cross sectional shape of which may be cylindrical to avoid contact with various surfaces and other mechanisms within the housing 102.

The tube 110 may carry narrower tubes that may be used for irrigation or suction. Water, saline, or other irrigation fluid may be delivered through a first narrower tube extended through the tube 110 as needed. Additionally, a second narrower tube may be extended through the tube 110 as needed, the second narrower tube being used for suction.

With regard to cutting tools 120, a rod or shaft having a tool configured to make an incision may also be selectively carried down the tube 110 as needed. A blade of the cutting tool 120 may be extended (at least initially) beyond the distal end of the tube 110. Once the incision has been made, the surgeon may trigger the cutting tool retraction mechanism to draw the cutting tool 120 back into the tube 110.

The distal end 112 of the tube 110 (which, after retraction of the cutting tool, is free from any obstruction due to the cutting tool 120) may then be used as a lumen for the irrigation tool 134 or the suction tool 138. In an extended position, a shaft of the blade of the cutting tool 120 may have sealed the distal end 112 of the tube 110 so that it was fluidically obstructed and not able to function as a fluid lumen, but with the cutting tool 120 retracted fluid communication may be established. The blade shaft of the cutting tool 120 may be retracted into the tube 110 to allow for a suction or irrigation conduit to form, or the blade of the cutting tool 120 may be drawn into the tube 110 to cover the tip of the blade for safety reasons.

Figure 2:
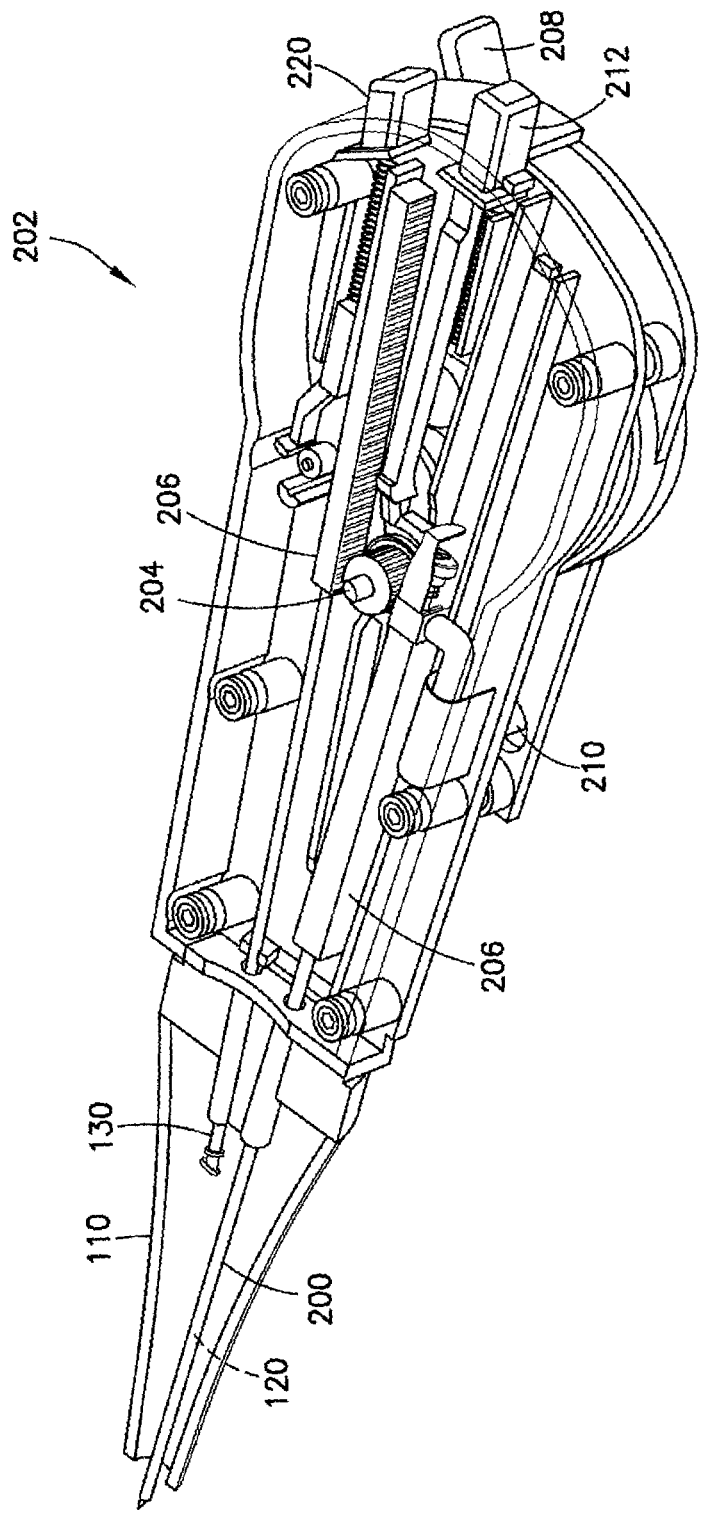
FIG. 2 is a perspective cutaway view of one example embodiment of a myringotomy device having a cutting tool deployed.
Figures 3, 4:
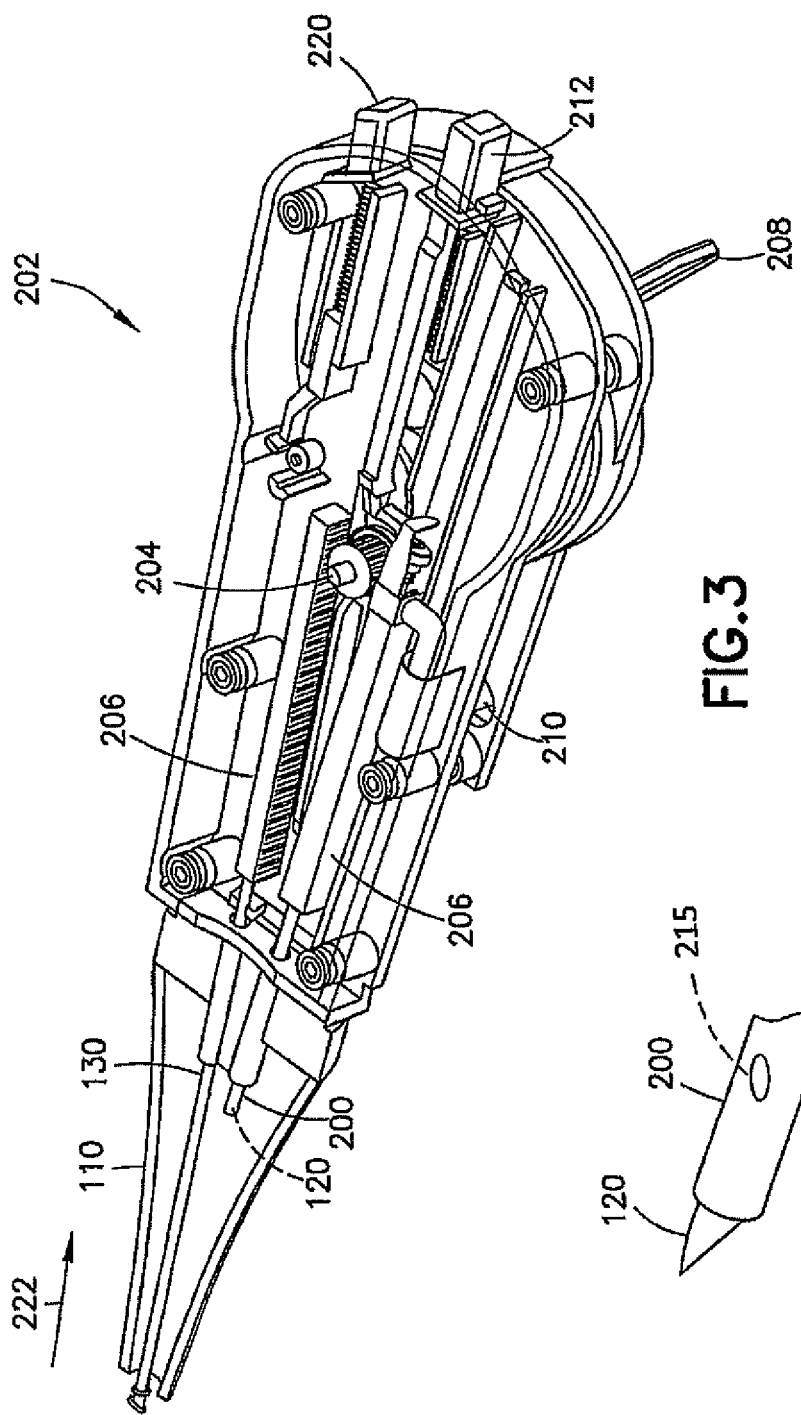
FIG. 3 is a perspective cutaway view of the device of FIG. 2 having a delivery tool deployed.
FIG. 4 is a perspective view of the cutting tool of the device of FIG. 2 deployed.

Referring now to FIGS. 2 and 3, one example embodiment of a housing of the device 100 is shown generally at 202. The housing 202 itself may operate as a handle and may include a pinion 204 configured to selectively and serially drive tools out of the distal end of the housing 202 and, for example, through the tube 110 and possibly out a common speculum. Each tool may have a carrier rack 206 coupled to or integrally formed therewith, the carrier rack 206 being configured to be engaged by the pinion 204. Each tool may be selected in the housing 202 via operation of a tool selection lever 208, which may be a toggle switch. As shown in FIG. 2, upon operation of the tool selection lever 208, the pinion 204 may be rotated in one direction to extend a first tool (e.g., the cutting tool 120) while simultaneously retracting a second tool (e.g., the delivery tool 130). As shown in FIG. 3, the tool selection lever 208 may then be switched to simultaneously extend the second tool (e.g., the delivery tool 130) and retract the first tool (e.g., the cutting tool 120). The first and second tools may be held at an angle from each other, although the tools may lie and actuate in a common plane. The device 100 is not limited to using a pinion 204 and carrier rack 206, however, as any suitable mechanism may be used to serially deliver the tools through the common speculum. Also, the tools may be secured to approximately one half of the inside of the housing 202 (and/or speculum) such that suitable portions of the housing 202 (and/or speculum) are free of the support mechanism, thereby preserving a line of sight as needed.

Referring now to FIGS. 2-4, a cutting operation may be carried out, for example, through a cannula 200 in which the cutting tool 120 may be located and through which suction may be applied. For suction, a suction hose may attach to a sleeve seal 210 on the housing 202. A cutting tool extension button 212 may be included on the housing 202 to selectively extend (and/or retract) the cutting tool 120 relative to the cannula 200 as needed.

When the cutting operation is carried out, the cutting tool 120 is extended from the cannula 200. When the cutting tool extension button 212 is pressed, a spring may be compressed and a blade of the cutting tool 120 advanced out of a distal end of the cannula 200. With the blade advanced, a weep hole 215 may be exposed, thus breaking the suction to allow the surgeon to carry out the cutting operation. When the cutting tool extension button 212 is pressed again, the blade may be retracted into the cannula 200 to cover the weep hole 215, thus allowing the suction to resume.

Upon switching the tool selection lever 208 away from the side of the housing 202 in which the cannula 200 and cutting tool 120 are located, the delivery tool 130 may be actuated. In doing so, the pinion 204 may be driven to retract the cannula 200 into the tube 110 and to advance the delivery tool 130 from the tube 110. Once the delivery tool 130 is advanced, as shown in FIG. 3, pushing a delivery tool button 220 may cause, for example, a mandrel to retract into the proximal direction, thereby stripping off an ear tube and leaving the ear tube in an incision in the patient's ear. The delivery tool button 220, however, may be configured to work only when the delivery tool 130 is in a suitable operating position. The device 100 is not so limited, however, as instead of a delivery tool 130, the housing 202 could be adapted to utilize other tools, such as, for example, an alligator forceps mechanism.

When the tool selection lever 208 switched, as shown in FIG. 3, the delivery tool 130 is retracted into the tube 110 as shown by arrow 222.

Figures 5A, 5B, 5C:
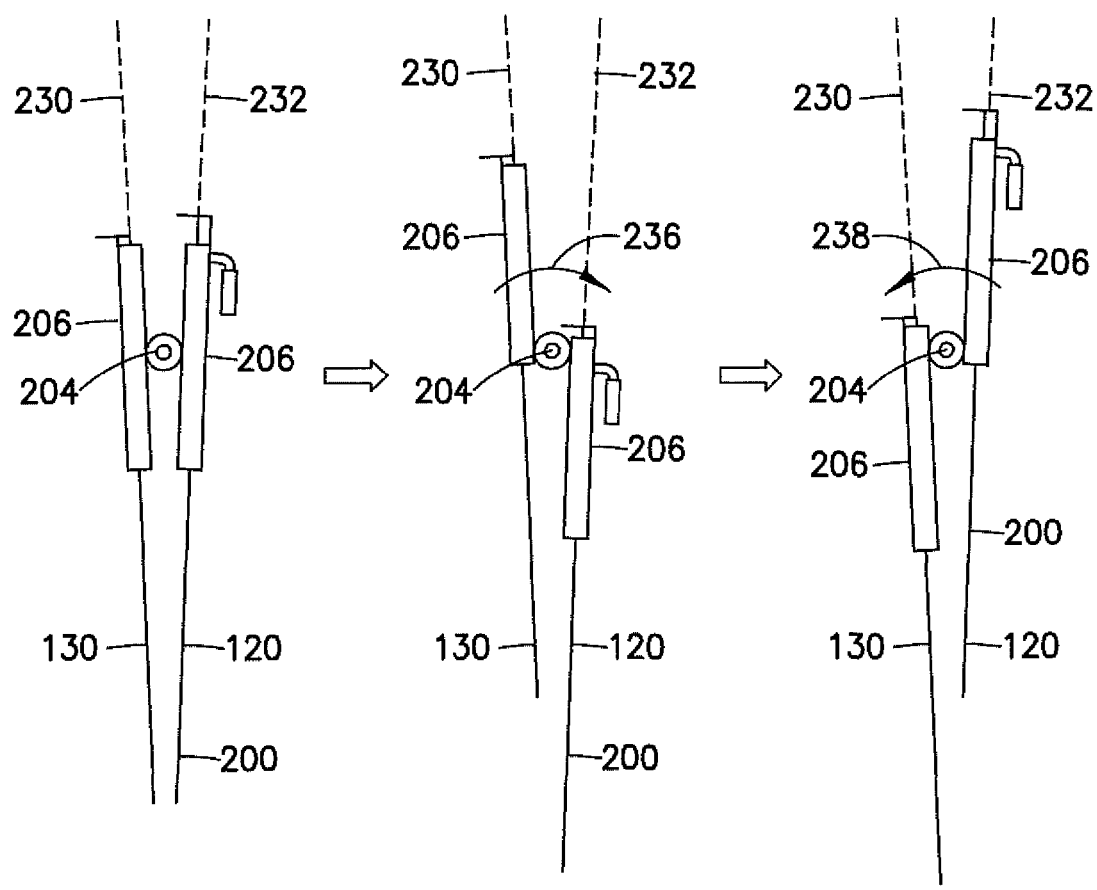
FIGS. 5A-5C are schematic representations of the device of FIG. 2 showing switching of the cutting and delivery tools.

Referring now to FIGS. 5A-5C, the switching of the cannula 200 and cutting tool 120 with the delivery tool 130 is shown. Both the cannula 200/cutting tool 120 combination and the delivery tool 130 may be mounted on different axes 230, 232, but they may be arranged to share the same mechanism that shuttles each tool down the tube 110. As shown in FIG. 5A, both the cannula 200/cutting tool 120 combination may be neutrally located in the housing 202. As shown in FIG. 5B, rotation of the pinion 204 in a first direction 236 may cause the cannula 200/cutting tool 120 to be deployed while the delivery tool 130 is moved in a proximal direction. As shown in FIG. 5C, rotation of the pinion 204 in a second direction 238 may cause the deployment of the delivery tool 130 and corresponding movement of the cannula 200/cutting tool 120 in the proximal direction.

Referring now to FIGS. 6A-6E, various cutting tools are shown. In FIG. 6A, the cutting tool 120 in a first position 300 is moved laterally to a second position 305 such that the cutting tool 120 makes a cut in a surface of the eardrum 400. In FIG. 6B, the cutting tool 120 may be used to make a scissor cut by inserting the cutting tool into the eardrum 400 and cutting from a first position 300 toward a second position 305, then reinserting the cutting tool 120 into the eardrum 400 and cutting from the second position 305 toward the first position 300. In FIG. 6C, the cutting tool 120 may be moved from a center position 310 to the first position 300, then back to the center position 310 and subsequently to the second position 305, thereby making an inverted scissor cut. In FIG. 6D, the cutting tool 120 may be used to puncture the eardrum 400 and spread the tissue thereof in outward directions.

In FIG. 6E, another embodiment of the cutting tool is shown at 620. The cutting tool 620 comprises a rod member 622 having an offset jag 624 having a sharpened edge 626. The offset jag 624 is used to puncture the eardrum 400, and the rod member 622 is rotated to cause the sharpened edge 626 to cut a hole in the eardrum 400.

Figure 7:
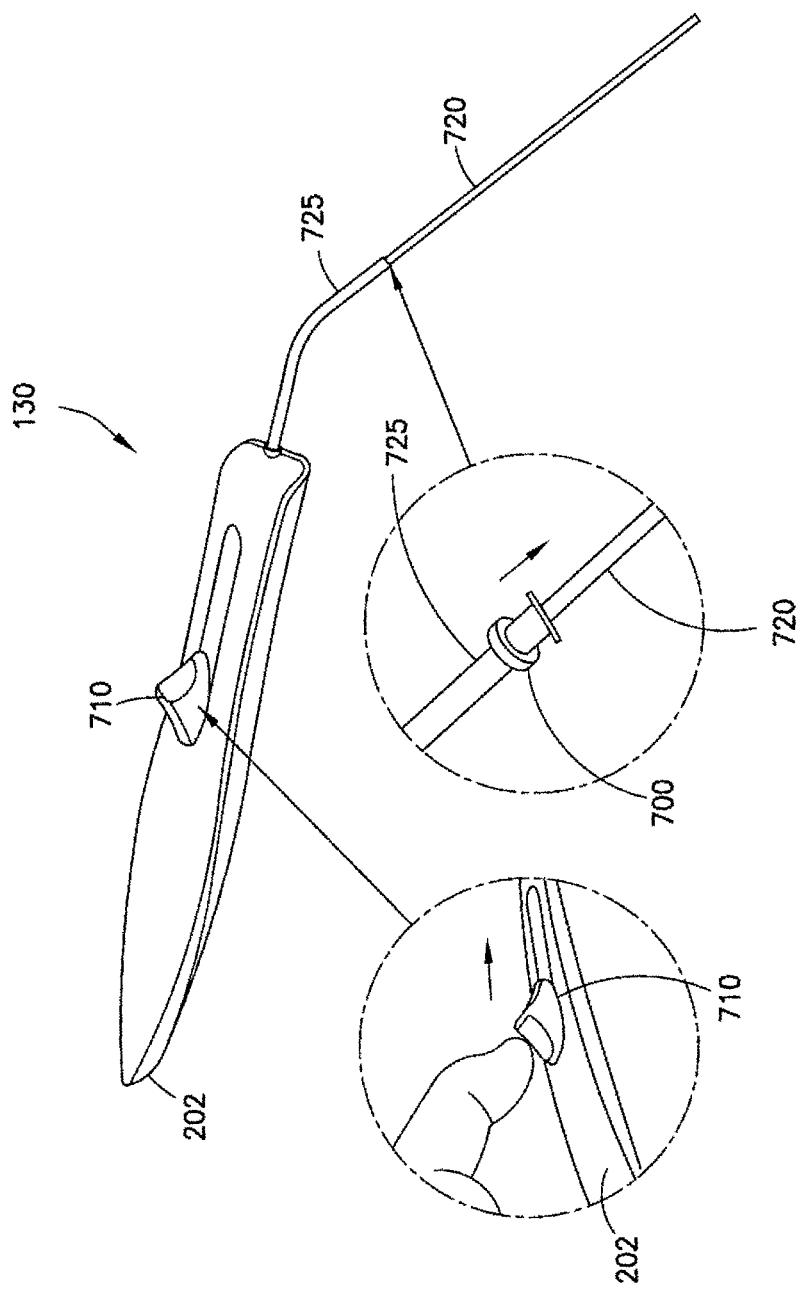
FIGS. 7 and 8 are representations of one example embodiment of a delivery tool for use with a myringotomy device.

Referring to FIG. 7, a delivery tool 130 that may be incorporated into the device 100 or used separately and in conjunction with other tools is shown. Once an incision is made in the eardrum 400, the delivery tool 130 is used to deliver the ear tube, which is shown at 700, to the incision and place the ear tube 700 such that one end of the ear tube 700 is in the outer ear and the other end of the ear tube 700 is in the middle ear, thus venting the tympanic cavity to the outer ear. The delivery tool 130 may comprises a trigger 710 mounted in the housing 202 (the housing 202 is not limited to the depicted design, as any configuration of the housing 202 may be used), with a flexible delivery tube 720 extending from the housing 202 and a sheath 725 slidably located over the delivery tube 720. The sheath 725 is operably coupled to the trigger 710 such that movement of the trigger 710 toward the distal end causes the sheath 725 to slide over the delivery tube 720. The ear tube 700 may be placed forward of the sheath 725. To effect a delivery of the ear tube 700 to an incision, the surgeon directs a distal end of the delivery tube 720 to the incision and moves the trigger 710 in a forward direction, thus causing the sheath 725 to slide the ear tube 700 over the delivery tube 720 and into the incision. The delivery tube 720 may then be retracted from the incision, and the ear tube 700 caused to be captured in the incision.

In using the delivery tool 130 in such a manner, the ear tube 700 may be introduced into the proximity of the incision on the delivery tube 720 configured as a central shaft (tube or rod) so that the surgeon than may insert the ear tube 700 into the incision and then by withdrawing the central shaft (the delivery tube 720 or other ear tube carrier shaft) the ear tube 700 is left behind in the incision. The sheath 725 may perform as a carrier for the ear tube 700. In this use, the delivery tube 720 may be a solid rod. For example if the delivery tube 720 is not used as a fluid lumen, then the delivery tube 720 may be a solid rod, and the distal end may also be sharp such that it functions as both a scalpel and an ear tube carrier. To improve the line of sight for the surgeon, the ear tube 700 may be carried, or chambered, a distance (possibly a considerable distance) proximal of the end of the delivery tube 720, which may be a hollow tube or a solid rod. This distance that the ear tube 700 is chambered from the distal end of the carrier tube may be given by the geometry of the ear tube 700. The distance may be 35-40 mm. The ear tube 700 may be chambered on the delivery tube 720 a distance from the distal end with the sheath 725 held proximal to the ear tube 700. The surgeon may deploy the ear tube 700 into the surgical site by moving the sheath 725 distally to force the ear tube 700 to the distal end of the delivery tube 720 and then off the distal end of the delivery tube 720. The movement of the ear tube 700 may be done in a single smooth movement, or in two discrete movements; the first to place the ear tube 700 at the very end of the delivery tube 720 and the second to push it off the end of the delivery tube 720. In one exemplary embodiment, the ear tube 700 may be chambered directly upon the sheath 725 that surrounds the delivery tube 720. The sheath 725 then carries the ear tube 700 thereon as the sheath 725 moves, rather than pushing the ear tube 700 along a stationary delivery tube 720.

Figure 8:
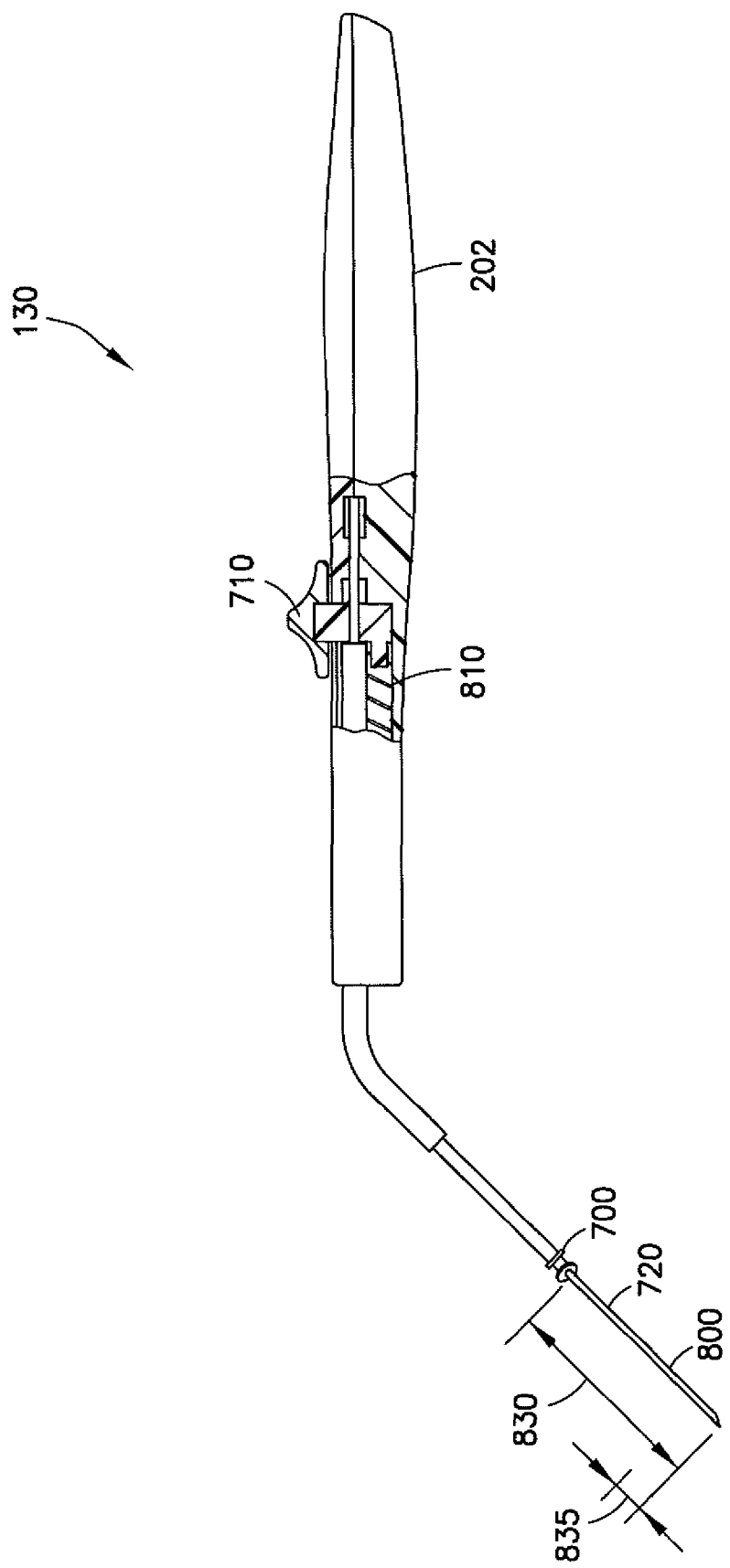

Referring to FIG. 8, in one example embodiment of the delivery tool 130, the delivery tube 720 may include a suction line 800. Furthermore, the trigger 710 may employ a spring 810 configured to indicate to the surgeon (e.g., by indicating a specified amount of force back to the surgeon) that the ear tube 700 is close to the end of the delivery tube 720. For example, when the ear tube 700 is more proximally located along the delivery tube 720, as indicated by distance 830, the spring 810 provides a softer feedback of force to the surgeon, whereas when the ear tube 700 is more distally located along the delivery tube 720, as indicated by distance 835, the spring 810 provides a harder feedback.

Figure 9:
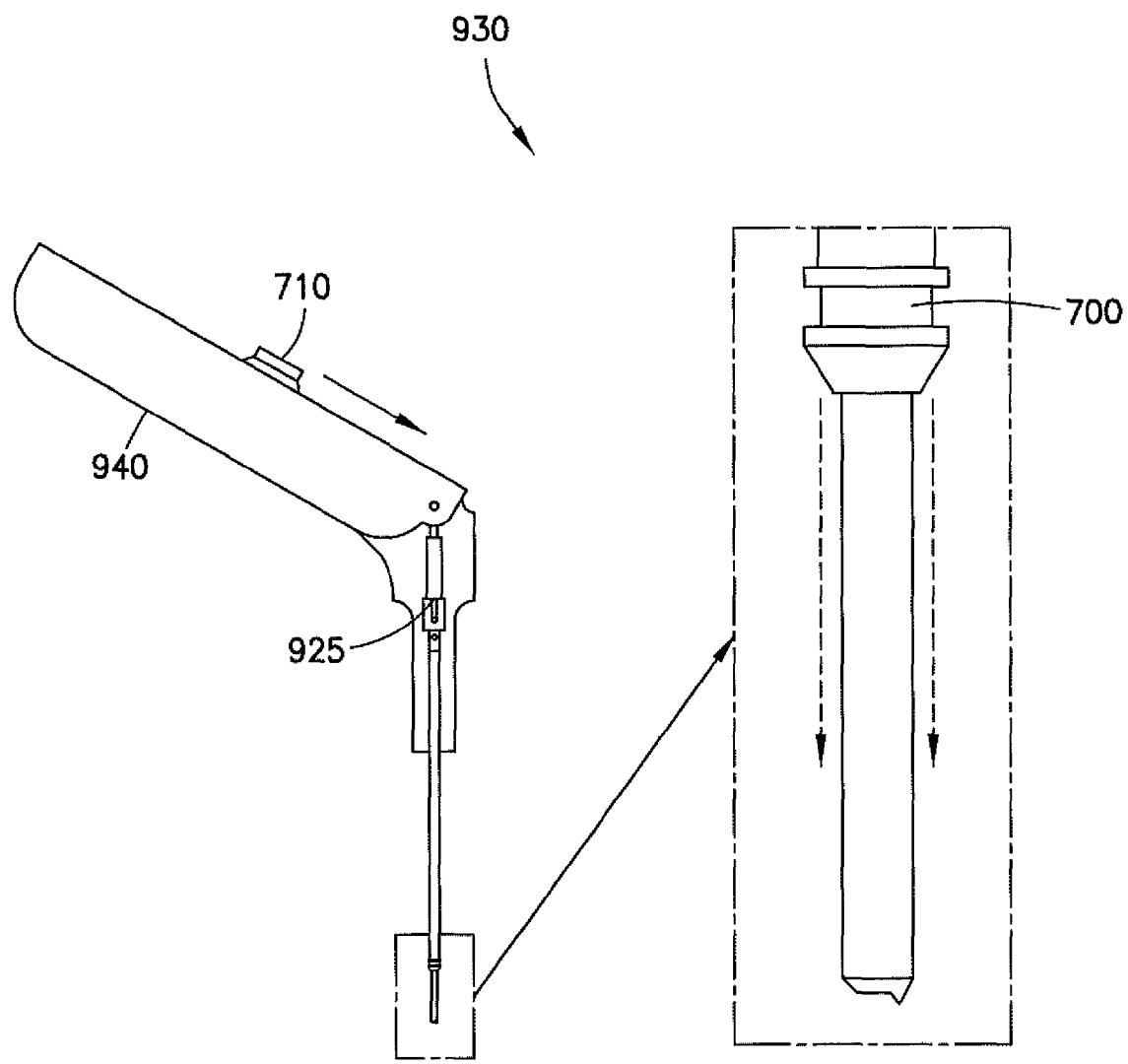
FIG. 9 is a schematic representation of another example embodiment of a delivery tool for use with a myringotomy device.

Referring to FIG. 9, another example embodiment of a delivery tool is shown at 930. Delivery tool 930 comprises a delivery tube 920 pivotally connected to a handle 940, with any suitable mechanism 925 configured to be actuated (such as by a trigger 710) to shuttle the ear tube 700 down the delivery tube 920 to the incision.

Figure 10:
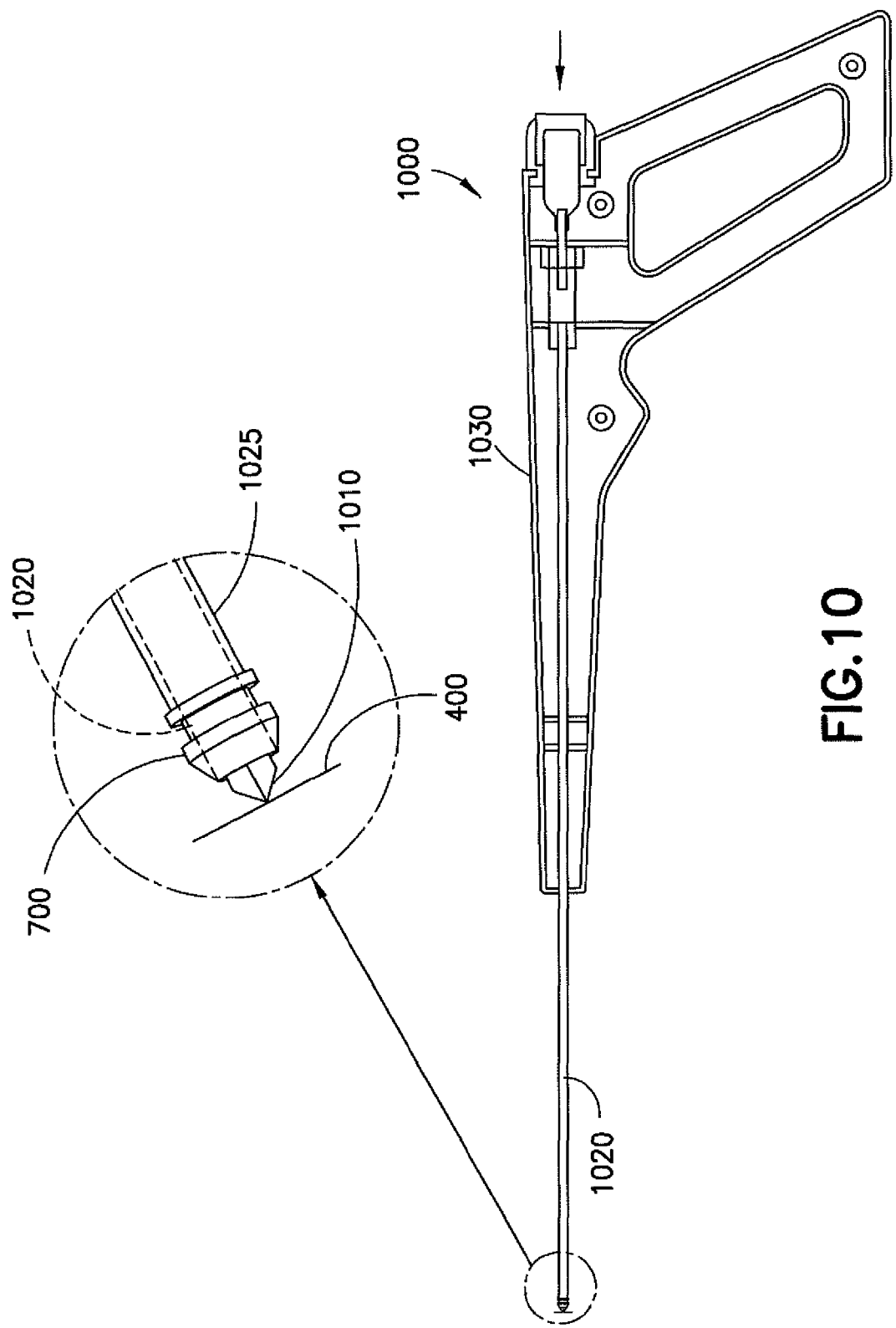
FIG. 10 is a schematic representation of one example embodiment of a combination cutting and delivery tool for use in a myringotomy procedure.

Referring to FIG. 10, one example embodiment of a combination of a cutting tool 120 and a delivery tool 130 is shown at 1000 and is hereinafter referred to as "combination tool 1000." In the combination tool 1000, the cutting tool 120 comprises a sharpened cannula or knife 1010, which is used to make an opening in a surface of the eardrum 400. The knife 1010 may be extendable from an elongated shaft in the form of a carrier tube 1020 depending from a handle 1030. An ear tube 700 may be slidable down the carrier tube 1020 to the surface of the eardrum 400.

The carrier tube 1020 may be axially fixed to the handle 1030. The knife 1010 is located inside the carrier tube 1020 and may be deployed to a distal position such that the blade of the knife 1010 at the distal end extends out the distal end of the carrier tube 1020. An ear tube 700 may be mounted on the outside of the carrier tube 1020 and in a position away from the distal end of the carrier tube 1020. There may be a pusher tube or sheath 1025 proximal of the ear tube 700 and which may be in direct contact with the proximal most edge of the ear tube 700, or there may be a gap between the sheath 1025 and the ear tube 700.

In one exemplary operation of the combination tool 1000, the surgeon may initially create an incision in a surface of the ear drum 400 using the knife 1010. After the incision is created, the surgeon may activate a trigger, button, or similar control on the handle 1030, and the knife 1010 may be retracted to remove the blade from the patient and to possibly also open up a fluid conduit. The surgeon may activate a trigger, button, or similar control to advance the pusher tube or sheath 1025 to drive the ear tube 700 to the distal end of the carrier tube 1020. With the ear tube 700 at this position the surgeon may then insert the ear tube 700 into the incision. The combination tool 1000 may include two discrete controls to activate the blade retraction and to advance the sheath 1025 to insert the ear tube 700. In the alternative, the combination tool 100 may include one control that actuations both the blade retraction and the sheath advancing mechanisms.

Figures 11A, 11B:
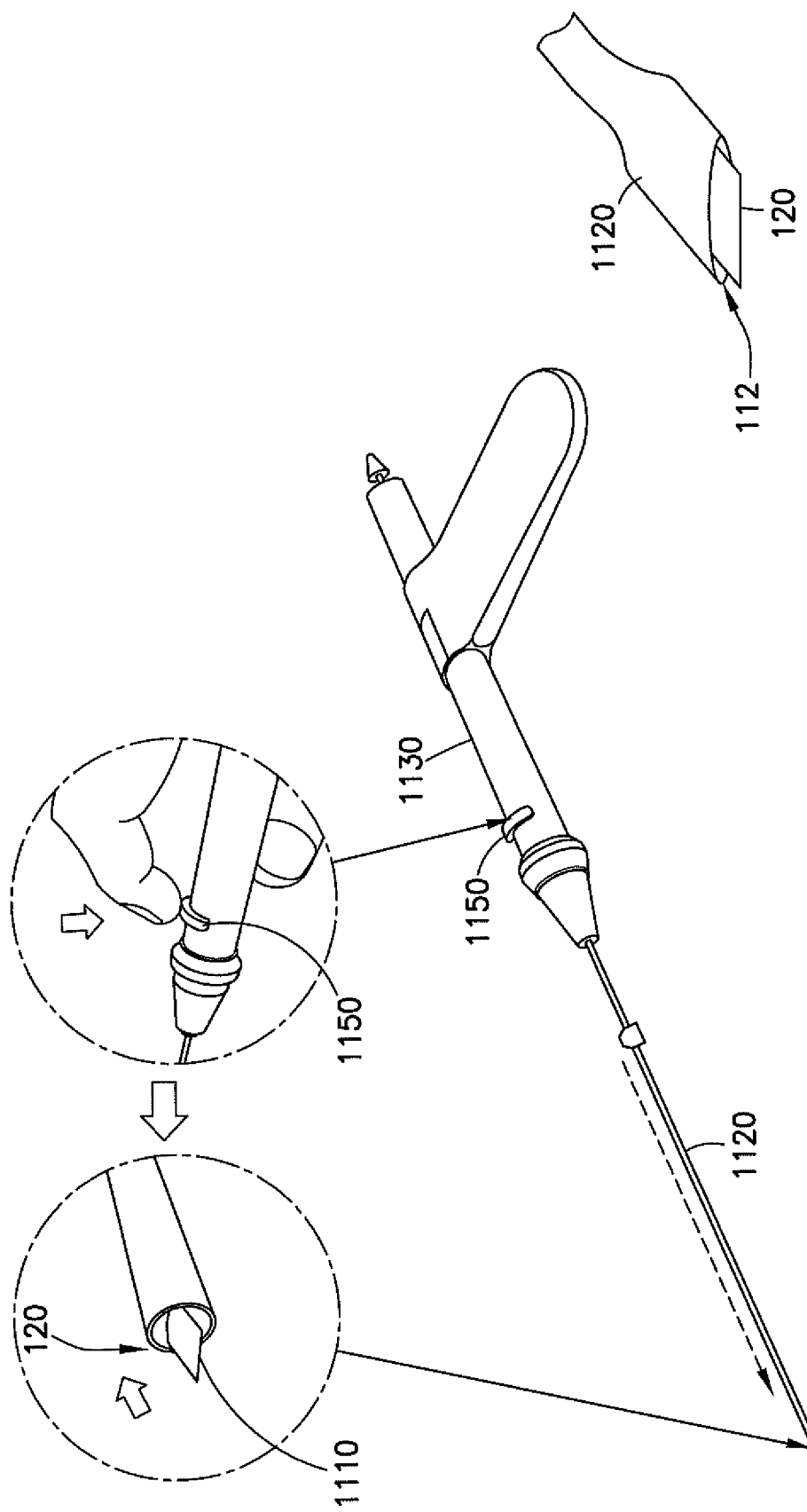
FIGS. 11A, 11B, and 12 are representations of other example embodiments of a combination cutting and delivery tool for use in a myringotomy procedure.
Figure 12:
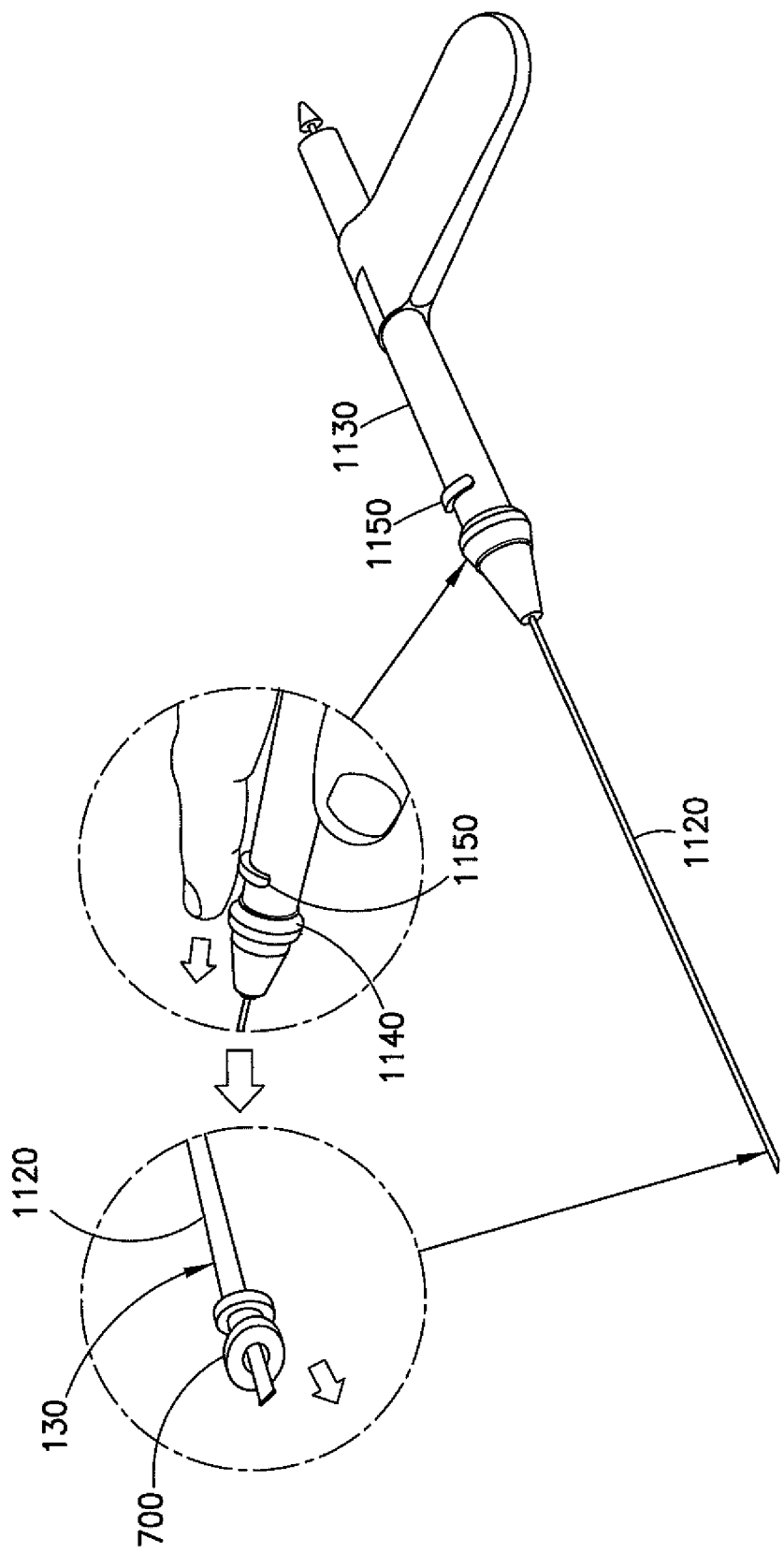

Referring now to FIGS. 11A, 11B, and 12, other example embodiments of combinations of a cutting tool 120 and a delivery tool 130 are shown at 1100 and are hereinafter referred to as "combination tool 1100." As shown in FIG. 11A, in the combination tool 1100, the cutting tool 120 comprises a knife 1110 extendable from a carrier tube 1120 depending from a handle 1130. Upon extending the knife 1110 from the carrier tube 1120, an incision can be made in an eardrum. The knife 1110 may be retractable into the carrier tube 1120 using any suitable mechanism (e.g., magnetics or suction). A button 1150 or other actuator on the handle 1130 may be operated to cause the knife 1110 to retract.

As shown in FIG. 11B, the distal end 112 of the carrier tube 1120 may be flattened from a round profile to a more elongated profile so that a blade of the cutting tool 120, which may be wider than a diameter of the main part of the tube 110 when the carrier tube 1120 has a circular cross section, can be retracted into the distal end 112 of the carrier tube 1120. The carrier tube 1120, when flattened on the distal end 112, may also allow for a smaller tube to be used, without decreasing the size of the blade of the cutting tool 120, so that the line of sight to the end of the carrier tube 1120 is improved.

As shown in FIG. 12, upon retraction of the knife 1110 into the carrier tube 1120 having either the flattened or rounded cross section, an ear tube 700 may be deployed by being shuttled down the outside surface of the carrier tube 1120 (e.g., via a sheath, pusher tube, or the like) and to a distal end of the carrier tube 1120. Depressing the button 1150 may not only unlock the knife 1110, as in some embodiments it may also allow the ear tube 700 to be rapidly shuttled to the distal end of the carrier tube 1120. More specifically, the button 1150 may act as a locking pawl for the knife 1110, and pushing the button 1150 may move the locking pawl and allow a magnetic propulsion to slide the sheath or pusher tube and the ear tube 700 farther down the carrier tube 1120 to put the ear tube 700 in close proximity to the incision (with the locking pawl out of the way, the knife 1120 can be retracted by suction and deposited into a holding area within the device). The surgeon may then control a final placement of the ear tube 700 into the incision, for example, by pushing a slide 1140 forward to push the ear tube 700 into the incision.

Figure 13:
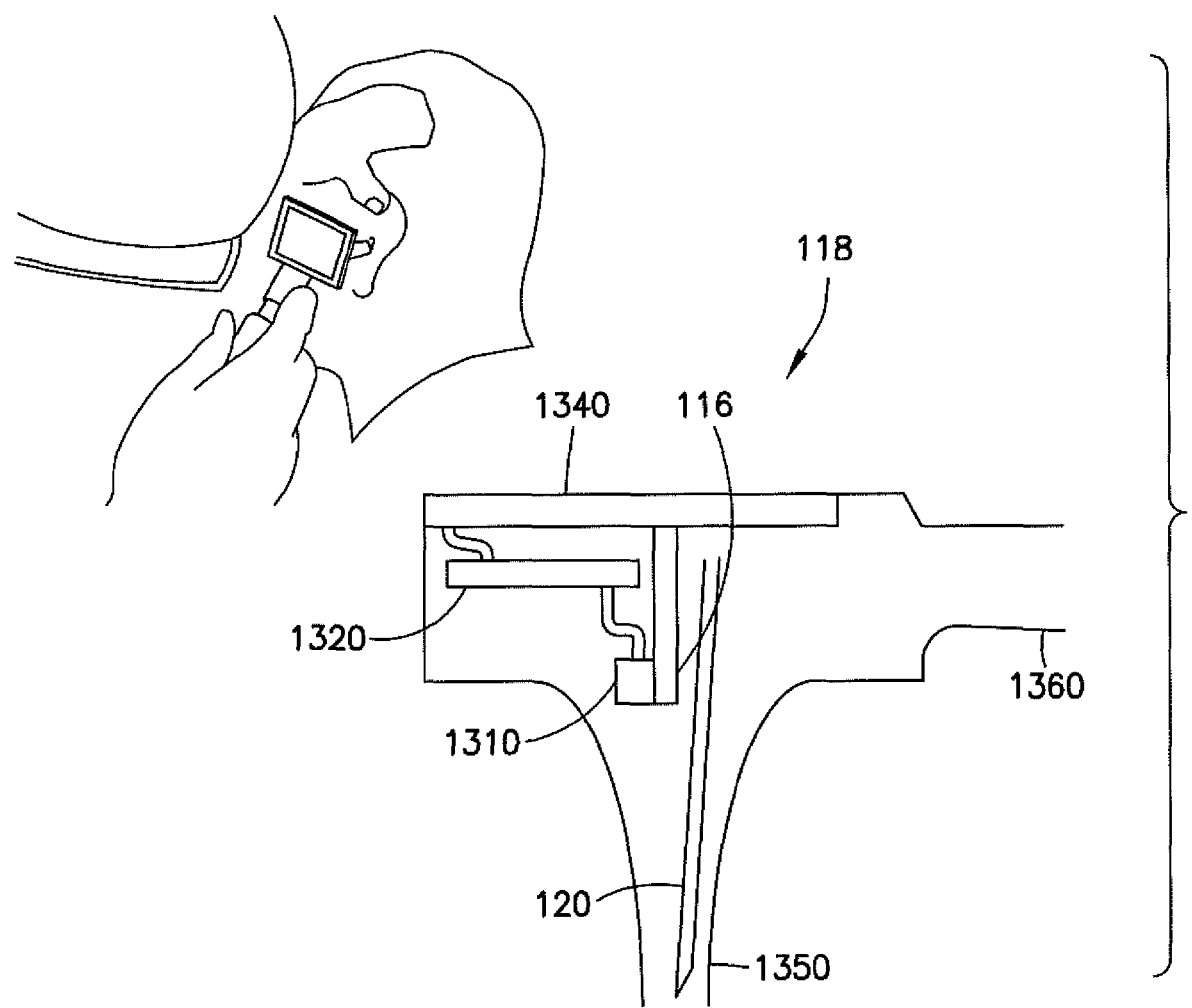
FIG. 13 is a schematic representation of one example embodiment of a viewing tool for use with a myringotomy device.

Referring now to FIG. 13, in any embodiment, a device 100 may have an integrated imaging system that includes the viewing tool 118. A suitable imaging system may include, for example, a camera 1310, a processor 1320 having software, and a display 1340, the camera 1310, the processor 1320, and the display 1340 being operably coupled together and mounted in a speculum 1350 having a handle 1360 attached thereto. The camera 1310 may comprise any suitable charge-coupled device (CCD) color video camera head. Any suitable cutting tool 120 (and/or delivery tool and/or combination of cutting tools 120 and delivery tools 130) may also be mounted in the speculum 1350. The illumination tool 116 may also be included in the speculum 1350, for example, in the form of one or more light emitting diodes (LEDs).

Figure 14:
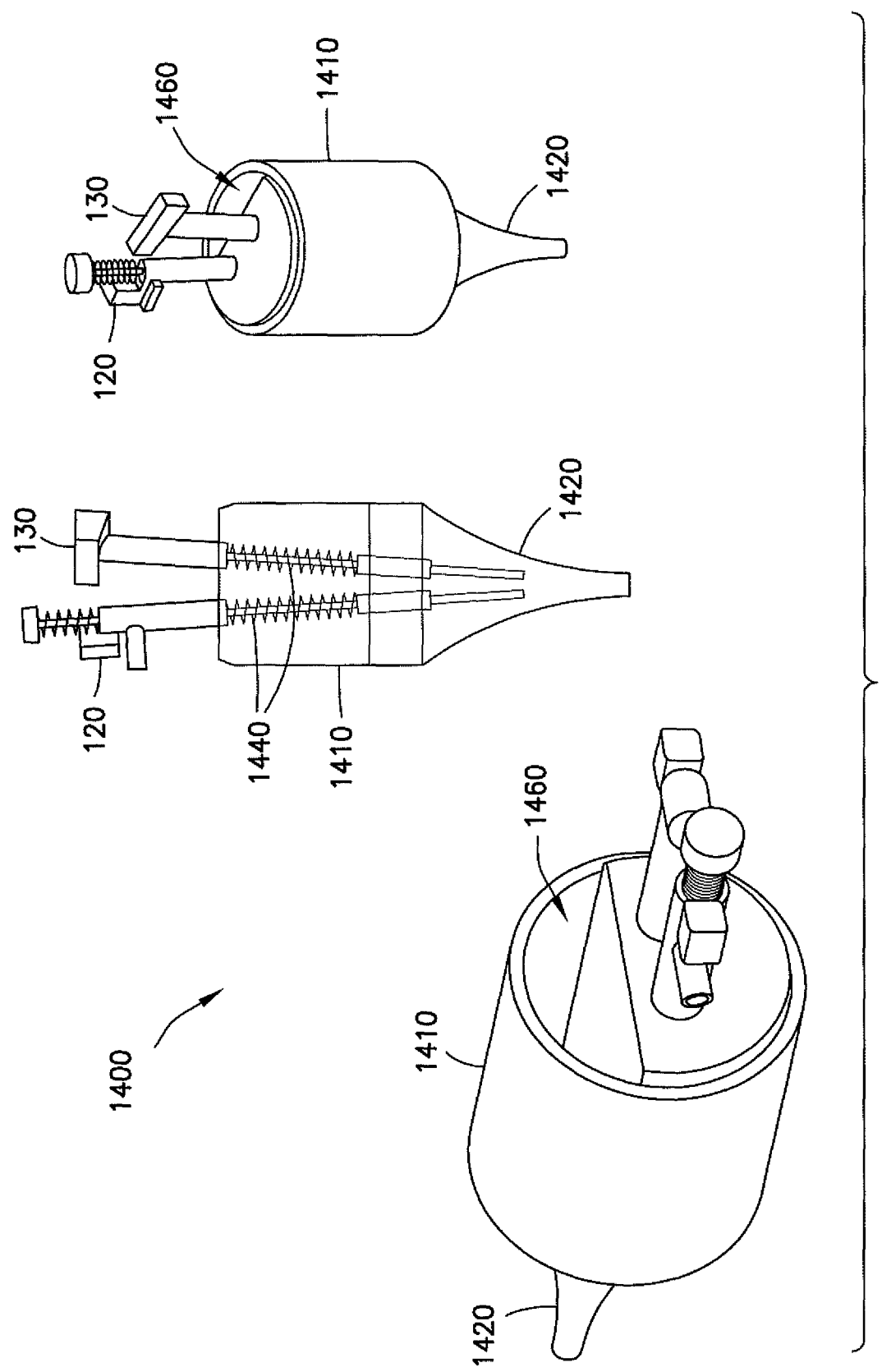
FIG. 14 is another example embodiment of a myringotomy device having spring tool deployment mechanisms.

Referring now to FIG. 14, another exemplary embodiment of a device is shown generally at 1400. The device 1400 comprises a body portion 1410 having a speculum 1420 depending from a distal end thereof and, for example, a cutting tool 120 and a delivery tool 130 mounted in the body portion 1410. The cutting tool 120 and/or the delivery tool 130 may be operable using springs 1440. The body portion 1410 may include an opening 1460 extending therethrough in order to preserve a line of sight.

Figure 15:
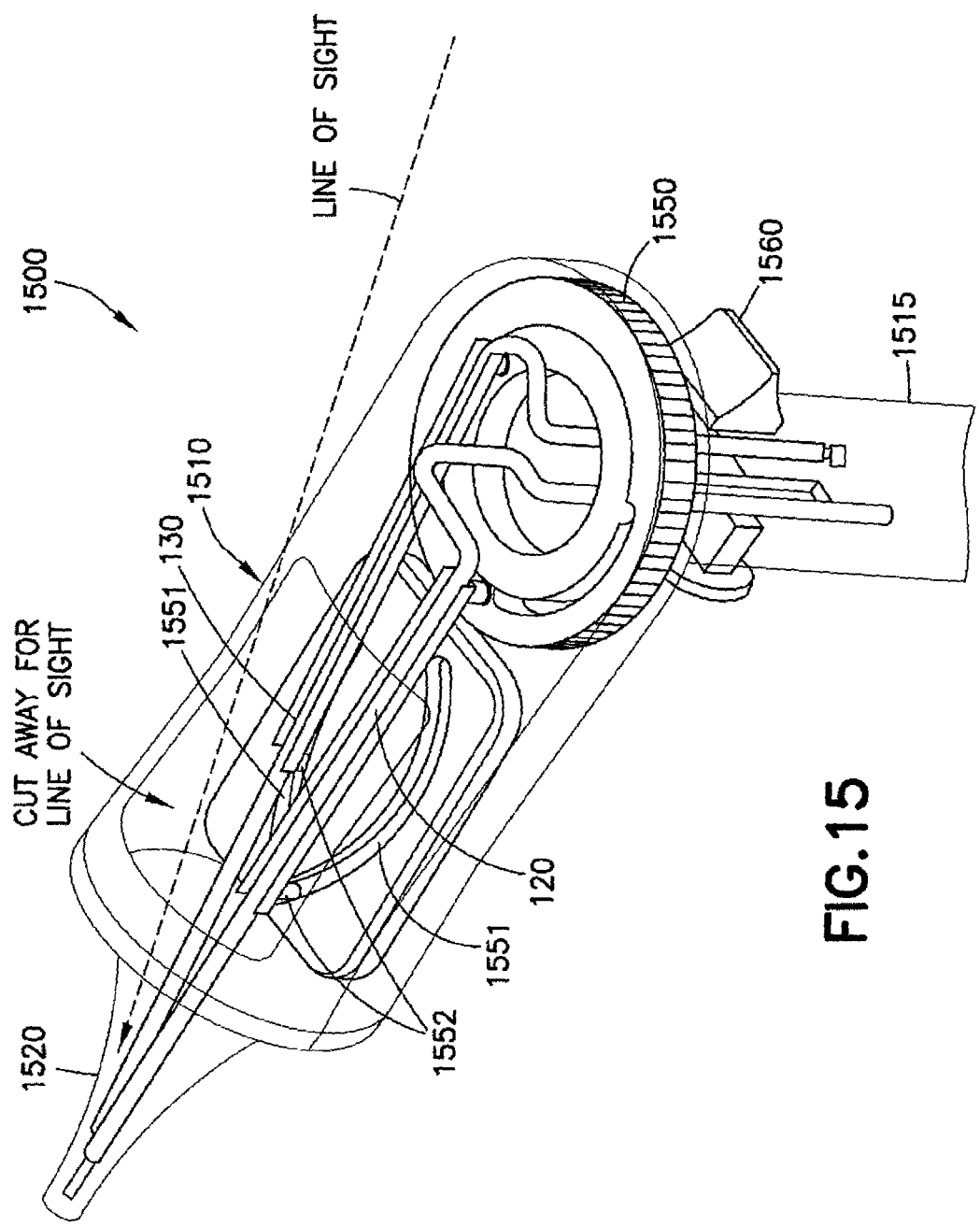
FIG. 15 is another example embodiment of a myringotomy device having a thumbwheel tool deployment mechanism.

Referring now to FIGS. 15 and 16A-16C, another exemplary embodiment of a device is shown generally at 1500. As shown in FIG. 15, the device 1500 may be a one-handed device (controllable by a surgeon using only one hand) and comprises a body portion 1510 in which two tool heads carrying distinct myringotomy tools (e.g., at least a cutting tool 120 and a delivery tool 130) may be mounted, a handle 1515 depending from the body portion 1510, and a speculum 1520 depending from a distal end of the body portion 1510. The cutting tool 120 and the delivery tool 130 may be coupled to and operable via a camming shuttle or thumbwheel 1550, which may be rotatable by the surgeon. In particular, the cutting tool 120 and the delivery tool 130 may be pivotally coupled to the same rotating shuttle at outward portions of the thumbwheel 1550 such that upon rotation of the thumbwheel 1550 by the surgeon, one of the cutting tool 120 and the delivery tool 130 may be driven along a cam path and advanced through the speculum 1520 and into the patient's ear while the other of the cutting tool 120 and the delivery tool 130 may be retracted and stowed in the body portion 1510. In the alternative, the end of each of the cutting tool 120 and the delivery tool 130 may connect to an individual shuttle. Distal to the caroming shuttle or thumbwheel 1550 there may be camming slots 1551 located forward of the cutting tool 120 and the delivery tool 130 into which locating pins 1552 on the respective cutting tool 120 and delivery tool 130 may travel. In this way, the rotation of the thumbwheel 1550 may both advance the tool and change its line of action. In particular, the line of action of one or both of the tools may be changed such that the tool is advanced along the axis of the speculum.

In device 1550, suction or magnetics may be incorporated to allow for retraction of the cutting tool 120. A push-type actuator 1560 may be used to deploy an ear tube from the delivery tool 130. Flexible cables may be incorporated into the device 1500 and coupled to actuators located on the handle 1515 to provide control for various other tools (illumination, suction, and the like). A portion of the body portion 1510 and the speculum 1520 may be cutaway to allow a clear line of sight to be maintained by the surgeon.

Figure 16C:
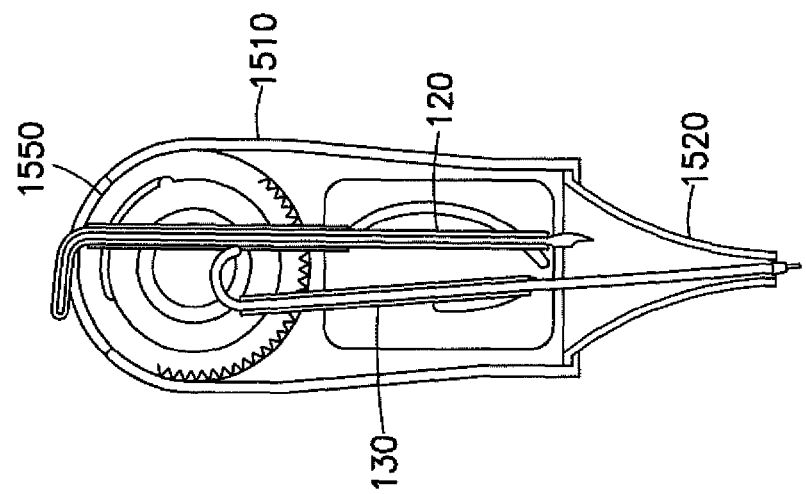
FIGS. 16A-16C are schematic representations of the thumbwheel tool deployment mechanism of the device of FIG. 15.
Figure 16B:
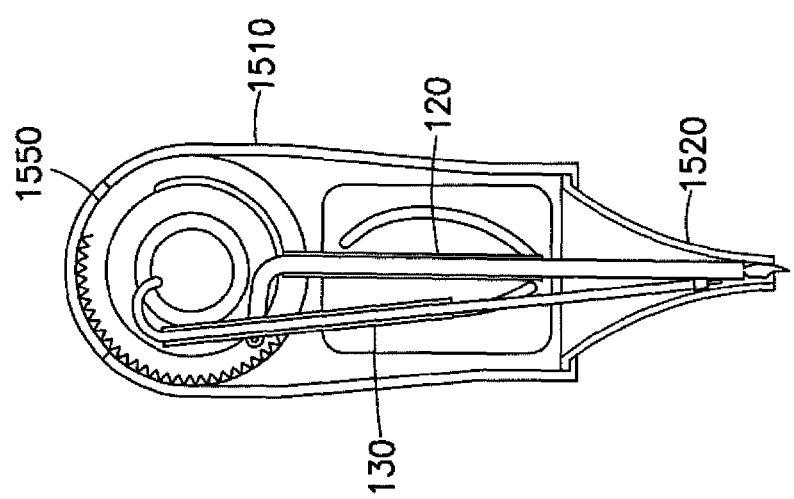
Figure 16A:
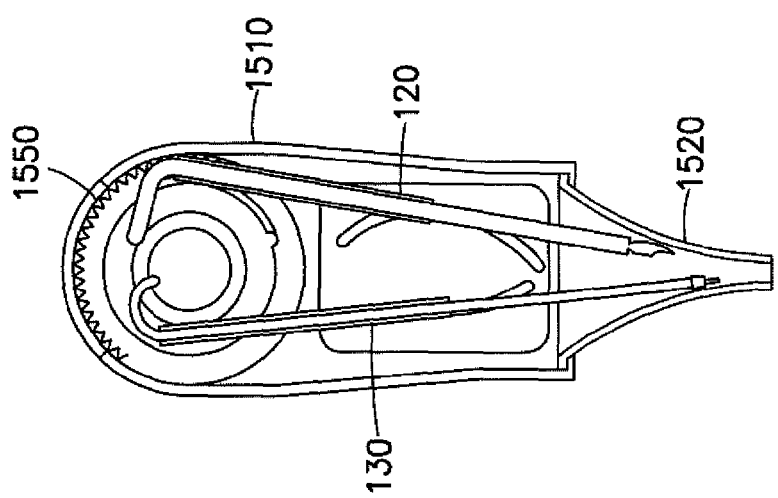

As shown in FIG. 16A, the cutting tool 120 and the delivery tool 130 may be stored in a "home" position in the body portion 1510. As shown in FIG. 16B, upon rotation of the thumbwheel 1550, the cutting tool 120 (or the suction or some other tool) may be advanced along the cam path into the speculum 1520. As shown in FIG. 16C, upon rotation of the thumbwheel 1550 in an opposite direction, the delivery tool 130 may be advanced along the cam path into the speculum 1520 while the cutting tool 120 is retracted.

Referring now to FIGS. 17A-17F, another exemplary embodiment of a device is shown generally at 1700. In device 1700, there may be multiple tool heads carried at the ends of flexible introducers, with each introducer having a thumb slider (sliding actuator) on a handle. The surgeon may advance any of the tools by sliding the sliding actuators in a forward direction.

As shown in FIG. 17A, the device 1700 is a manually operated knife comprising a manifold 1710 to which a handle 1720 may be pivotally mounted. A speculum 1730 may depend from a distal end of the manifold 1710. The manifold 1710 may have a pivot center 1740 for controlling a depth and a length of an incision. The pivot center 1740, in conjunction with the diameter of the speculum 1730, may control an arc length for the incision. More specifically, pivoting the knife from one side of the speculum 1730 to the other may produce a cut of a known length (e.g., about 1.7 millimeters (mm)), assuming a speculum 1730 having a 4 mm diameter. There may also be a slot on a side surface of the shaft, the knife being movable in the slot to control a depth of the incision.

As shown in FIG. 17B, a rigid suction lumen or suction cannula 1750 may extend through the handle 1720 to the manifold 1710 and into the speculum 1730 and may be controllable (e.g., advanced and retracted from the speculum 1730) via operable connection to a first sliding actuator 1755. The suction cannula 1750 may be coupled to a flexible tube that connects the suction cannula 1750 to a suction source. A sealing sleeve 1751 (which may be rubber) having a weep hole 1755 on an underside thereof is mounted on the suction cannula 1750 such that when the suction cannula 1750 is advanced, the suction cannula 1750 is pivoted down to the deploy position and the sealing sleeve 1751 engages a surface within the handle 1720 to block the weep hole 1775, thereby invoking the suction. In the alternative, the suction cannula 1750 may be connected to a suction port such that when the lumen or cannula is advanced, the suction cannula 1750 connects to a fitting that is connected to the suction source, and when the suction cannula 1750 is retracted the connection with the suction source is broken (the suction is thereby not connected between the suction source and the distal tip of the suction cannula 1750). This may have the advantage of having the suction cannula 1750 not performing suction when the cannula 1750 is retracted. Additionally, this design may reduce the auditory shock to the patient. That is, in this design the suction source may stay connected at all times and produce a "white noise" suction sound whether the suction at the distal tip is operational or not. In this way, the patient might not be startled by a sudden sound when the suction would, otherwise, be turned on or off.

Ear tube insertion forceps 1760 may also extend from the handle 1720, through the manifold 1710 and into the speculum 1730 and may be controllable via operable connection of a flexible introducer or bar linkage to a second sliding actuator 1765. Operation of the second sliding actuator 1765 allows the forceps to move between operating and stowed positions in the handle 1720.

In operation of the first sliding actuator 1755 to control the suction cannula 1750, upon rotation to an operating position in embodiments employing the weep hole 1775, the weep hole 1775 may be plugged to allow the suction to engage. Operation of the second sliding actuator 1765 accordingly moves another flexible introducer and deploys the forceps 1760 into the operating position. A trigger 1770 on the handle may be used to open the jaws of the forceps 1760, thereby releasing an ear tube 700 into an incision.

Figure 17C:
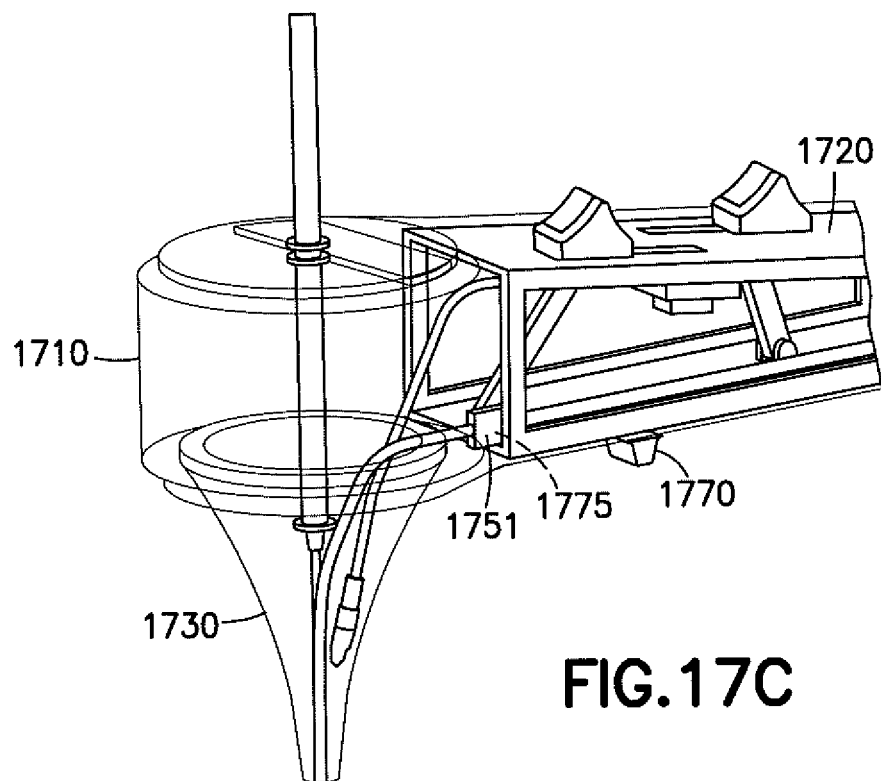

As shown in FIG. 17C, the suction cannula 1750 can be rotated into an operating position. Manipulating the first sliding actuator 1755 may advance the suction cannula 1750. When the suction cannula 1750 is in the operating position, the sealing sleeve 1751 compresses on an inner surface of the housing and the weep hole 1775 is plugged to allow the suction to engage.

Figure 17D:
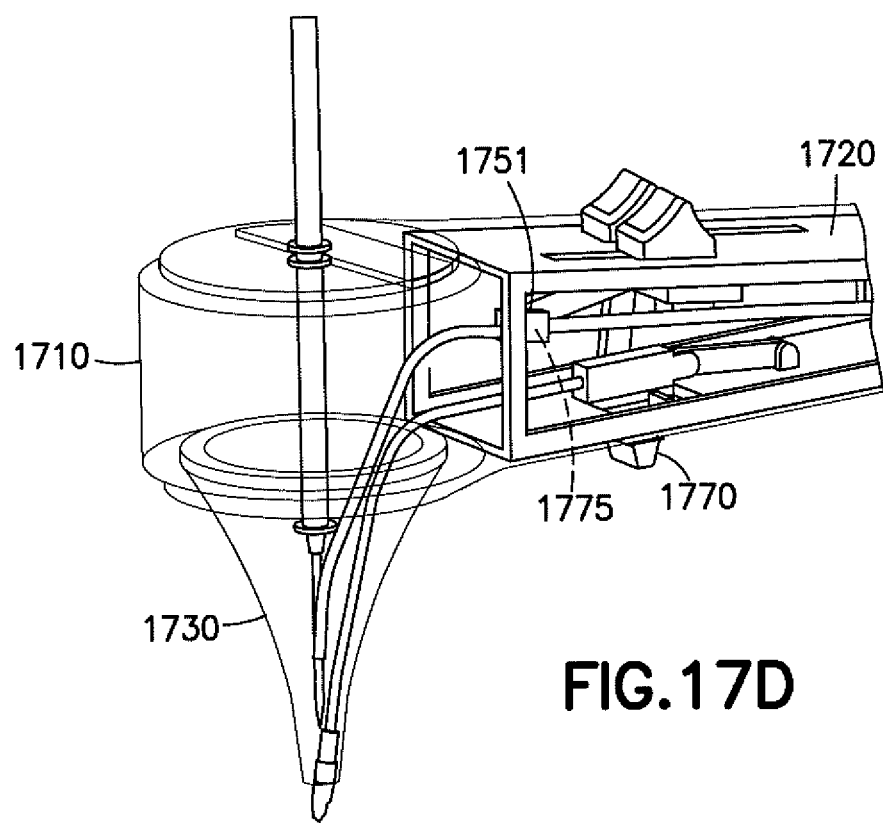

As shown in FIG. 17D, the forceps 1760 can be rotated into the operating position. Manipulating the second sliding actuator 1765 may advance the forceps 1760. Sliding the trigger 1770 on the handle 1720 accordingly opens the jaws of the forceps 1760 and releases the ear tube 700 into the incision.

Figure 17F:
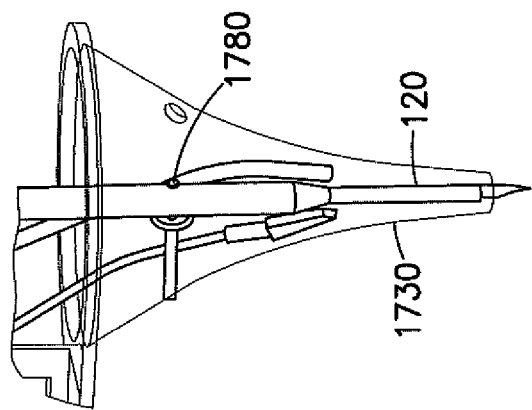
Figure 17E:
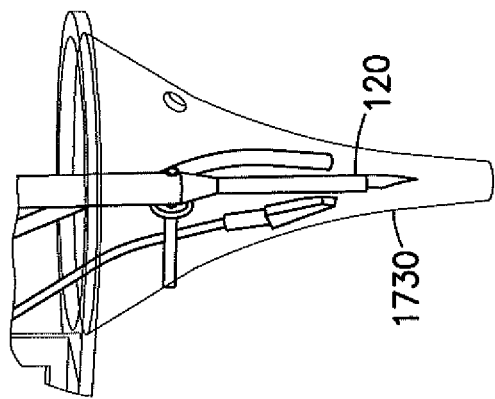

As shown in FIG. 17E, a cutting tool 120 in the form of the manually operated knife is shown in the stowed position. The cutting tool 120 is shown in the operating position and prepared for making an incision. As shown in FIG. 17F, the cutting tool 120 includes a slot which engages a pin 1780 on the speculum 1730. When deployed, the knife of the cutting tool 120 pivots around the pin 1780.

Figure 18:
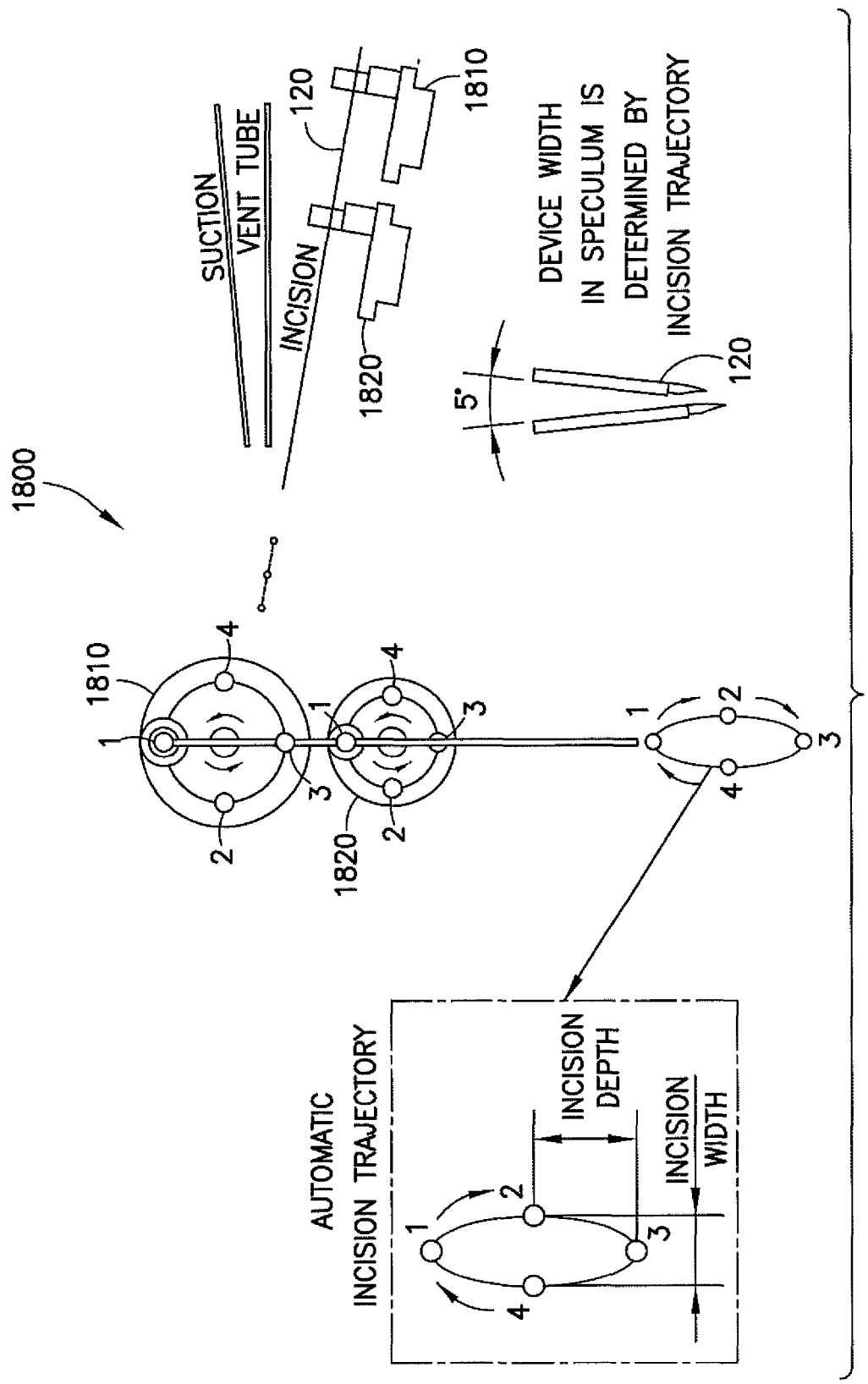
FIG. 18 is a schematic representation of an example embodiment of deploying a cutting tool from a myringotomy device.

Referring now to FIG. 18, one exemplary embodiment of the mounting of a cutting tool 120 is shown generally at 1800. The cutting tool 120 may be mounted to two corotating wheels 1810, 1820 configured to, upon rotation, provide a prescribed motion to the tip of the cutting tool 120. For example, the two wheels 1810, 1820 may impart a 5 degree sweep of the cutting tool 120 to provide a single-direction straight line incision while controlling the depth and width while not interfering with the positions and/or operations of other tools. As shown, the cutting tool 120 may be coupled to the each wheel 1810, 1820 such that at Position 1, the cutting tool 120 is in a retracted position. When the cutting tool 120 is positioned to make an incision, a proximal end of the cutting tool 120 is in Position 2, and a distal end (the tip) of the cutting tool is at the surface to be cut. Upon rotating the wheels 1810, 1820 to Position 3, the cutting tool 120 is plunged past the surface to be cut to its maximum depth. Upon rotating the wheels 1810, 1820 to Position 4, the tip of the cutting tool 120 is retracted to the surface. Upon rotating the wheels 1810, 1820 back to Position 1, the cutting tool 120 is retracted. The length of an incision is determined by a trajectory of the tip of the cutting tool 120, which is in turn determined by the dimensions of the wheels 1810, 1820. This mechanism may produce incisions of highly repeatable length and depth.

Figure 19A:
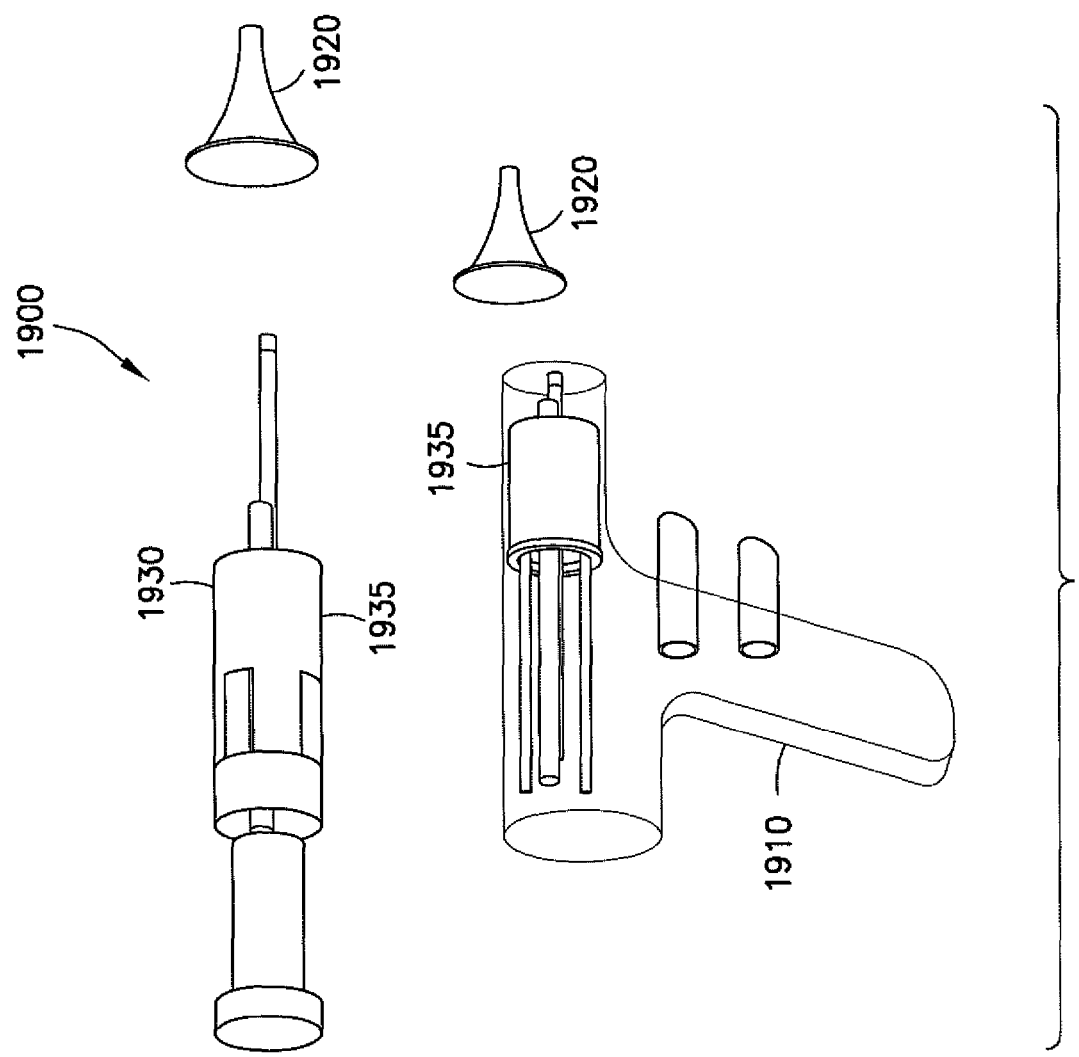
FIGS. 19A-19E are representations of another example embodiment of a myringotomy device having a carousel-type tool deployment mechanism.

Referring now to FIGS. 19A-19E, another exemplary embodiment of a device is shown generally at 1900. As shown in FIG. 19A, device 1900 comprises a body portion having a handle 1910 depending therefrom and a speculum 1920 located at a distal end of the body portion 1930. In the body portion 1930, a plurality of tools may be rotatably located in a barrel or carousel 1935.

Figure 19B:
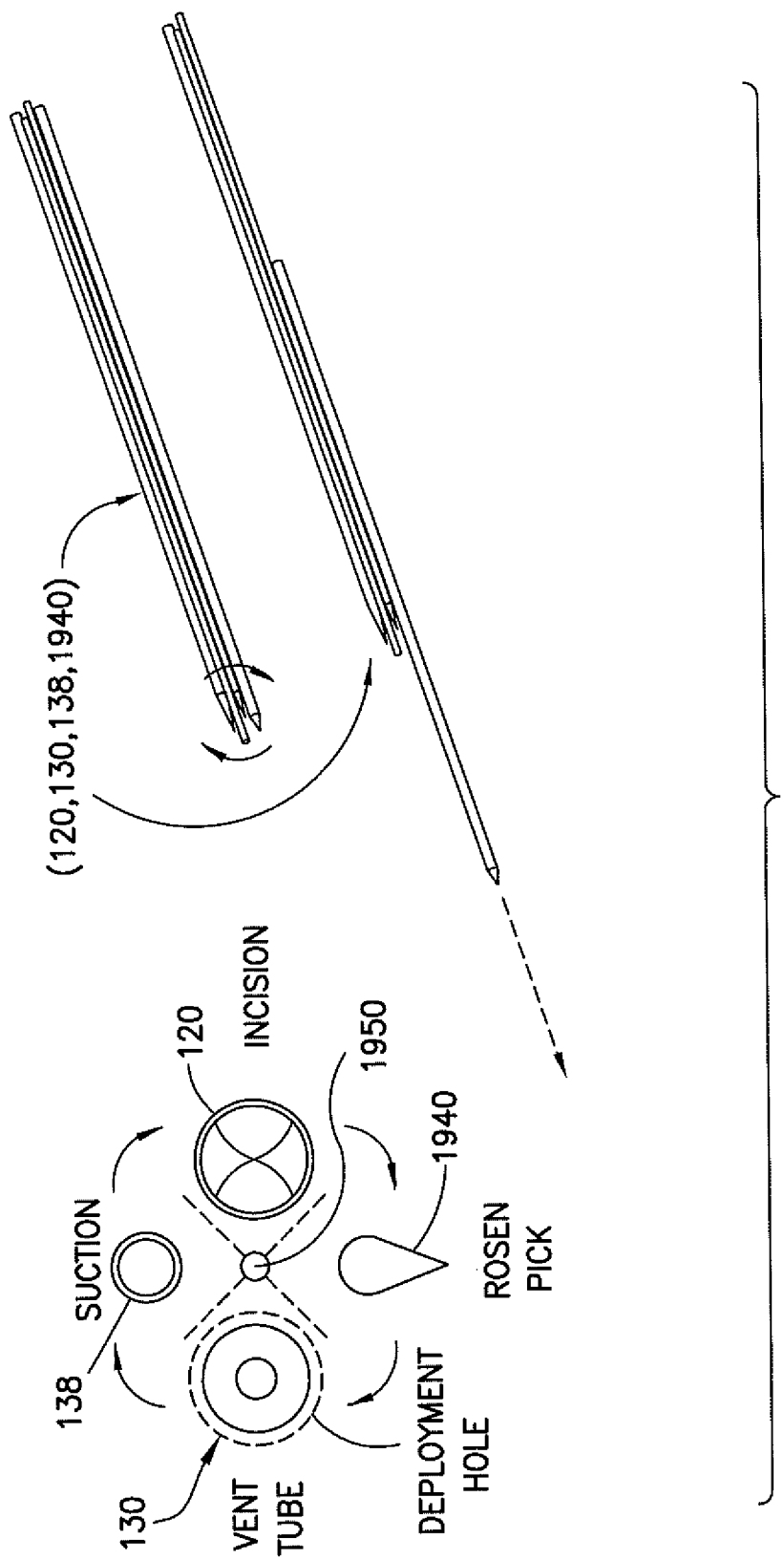

As shown in FIG. 19B, the carousel 1935 may include four tools (e.g., a delivery tool 130, a suction tool 138, a cutting tool 120, and a rosen pick 1940) that rotate around a common axis 1950 to deliver a desired tool to a deployment position. One quadrant may be configured to activate a selected tool and to shuttle it into a position for use. In any configuration, a line of action of a tool in the deployment position may be coaxial with the speculum, or the center axis of the carousel may be coaxial with the speculum.

Figure 19C:
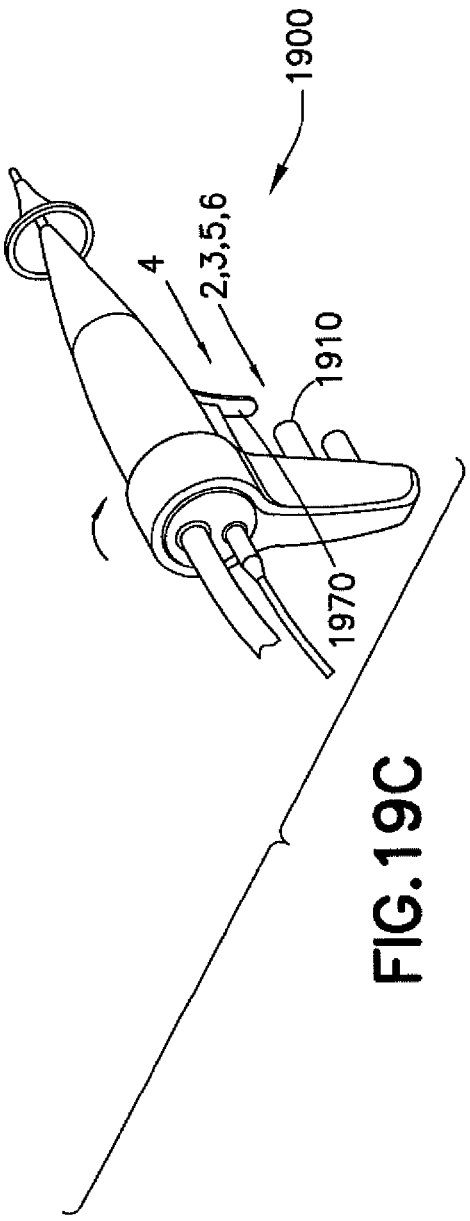

As shown in FIG. 19C, a graphic showing an activation of the tools of device 1900 is shown. The device 1900 is used to sight an eardrum 400 (Step 1). In Step 2, an actuator button 1960 is pressed to deploy a corresponding tool. In Step 3, the actuator button 1910 is pressed to retract the deployed tool. In Step 4, a trigger 1970 may be pulled to rotate the carousel to bring a second tool into position for use. In Step 5, the suction tool may be activated. In Step 6, an ear tube 700 may be released from the device 1900 and placed into the eardrum.

Figure 19D:
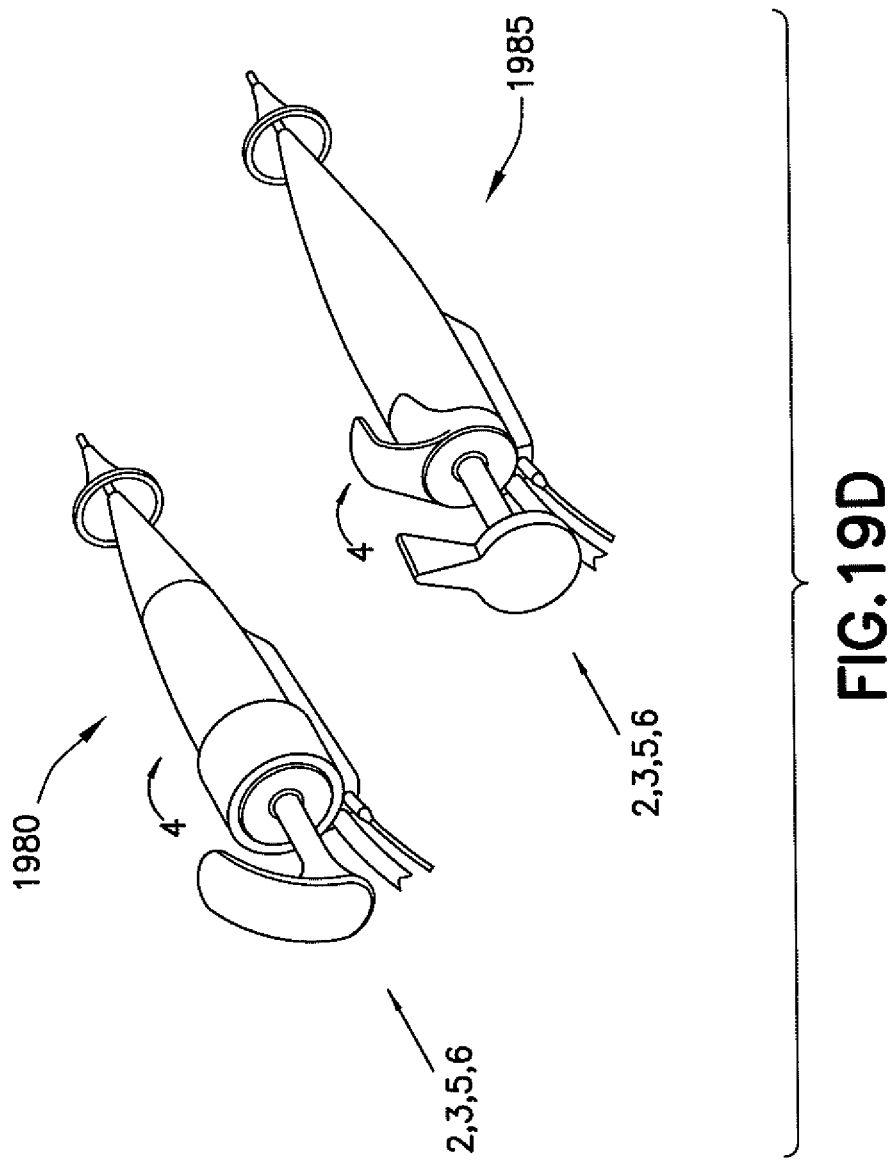

As shown in FIG. 19D, the same Steps as indicated above may be carried out using devices 1980, 1985 having controls as shown.

Figure 19E:
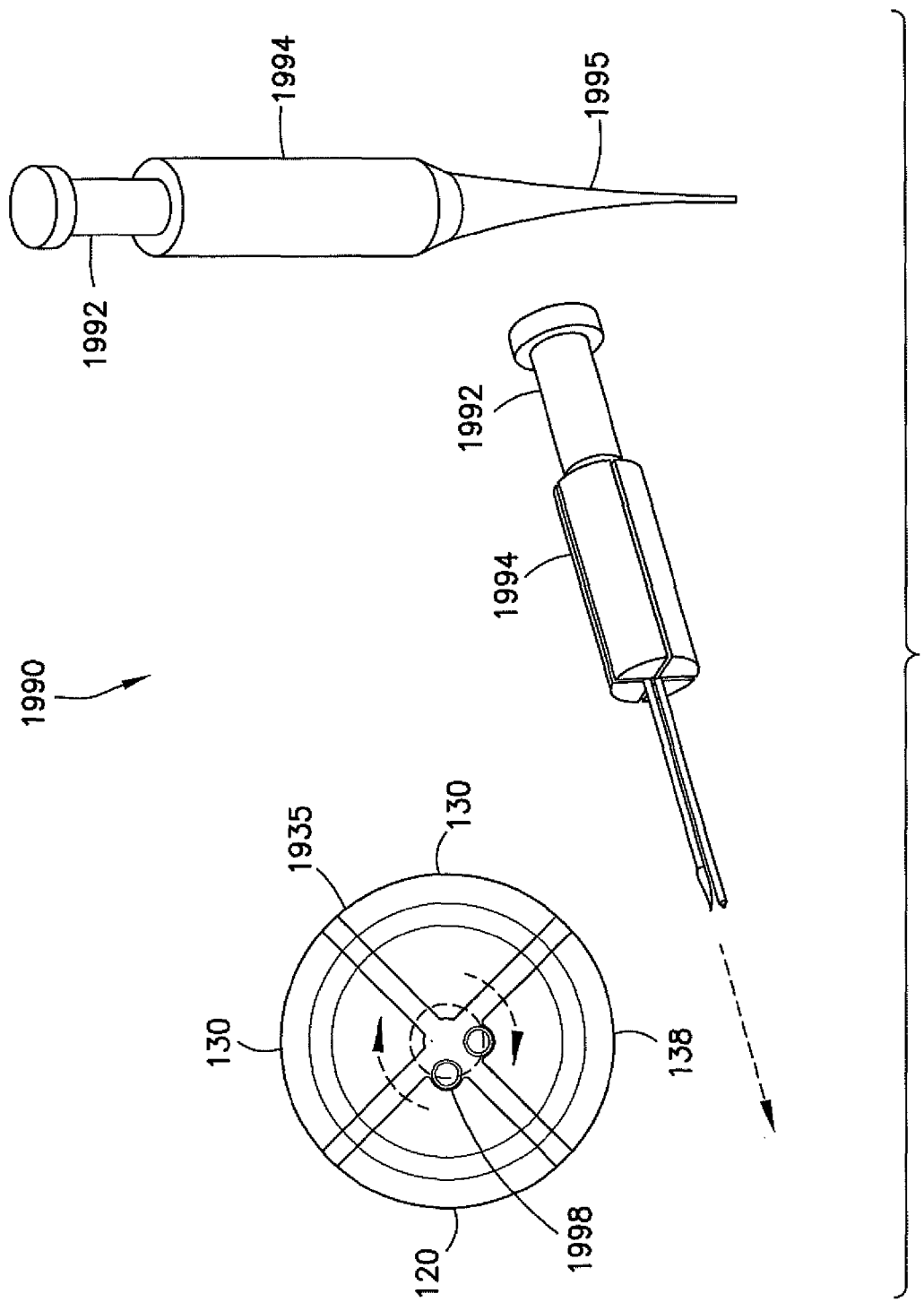

As shown in FIG. 19E, another exemplary embodiment of a device 1990 employing a carousel-type tool rotation mechanism is shown. Such a device 1990 uses a tool spin and activation knob 1992 that allows the surgeon to rotate to a specific tool and to then push it down for deployment from a body portion 1994 and through an outlet port 1998 in a speculum 1995 while keeping the device out of the line of sight. The four quadrants of the carousel 1935 allow for a cutting tool 120, a suction tool 138, and delivery tools 130 that may deliver two styles of eardrum tubes 700, depending upon the preference of the surgeon.

Figure 20A:
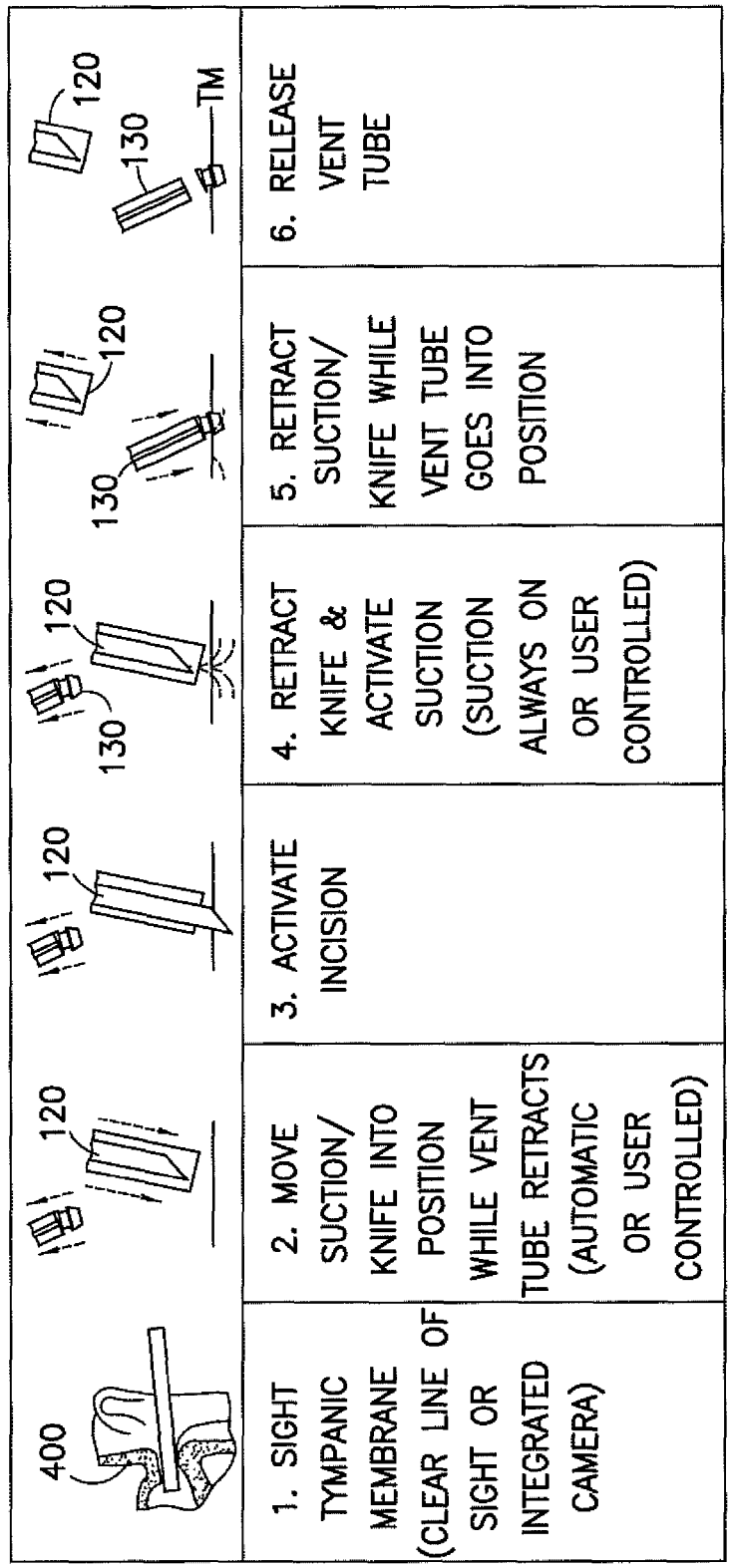
FIGS. 20A-20E are schematic representations of example operations of a myringotomy device.

Referring now to FIGS. 20A-20E, one exemplary embodiment of the operation of a device is shown generally at 2000. In operating the device 2000, as shown in FIG. 20A, the eardrum 400 is sighted (Step 1) for example on a display 2010, and the suction tool and/or cutting tool 120 is moved into position (Step 2). The cutting tool 120 is then activated to make the incision (Step 3). In Step 4, the cutting tool 120 is retracted and the suction is activated. In Step 5, the suction and cutting tool 120 are removed, and the delivery tool 130 is maneuvered into position. In Step 6, the ear tube 700 is released from the delivery tool 130 and inserted into the incision.

Figure 20B:
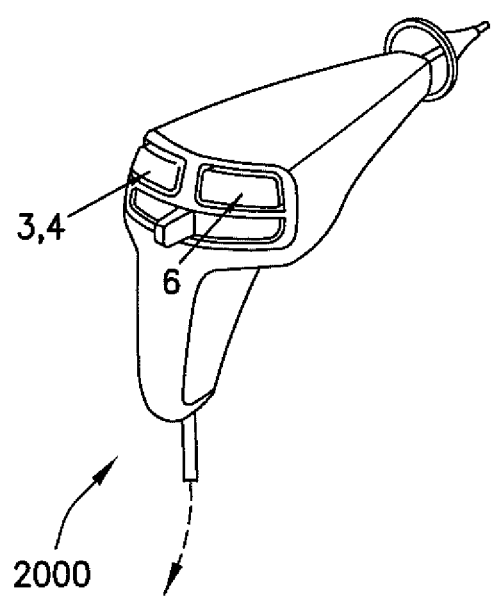
Figure 20C:
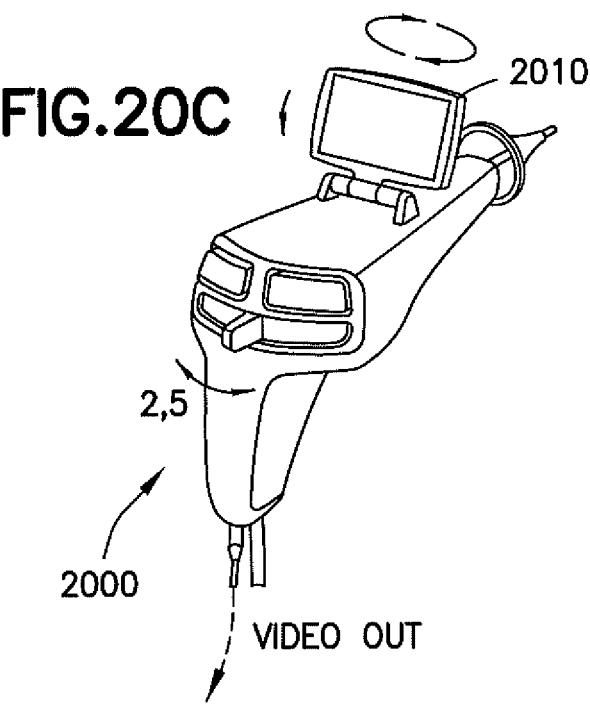
Figure 20E:
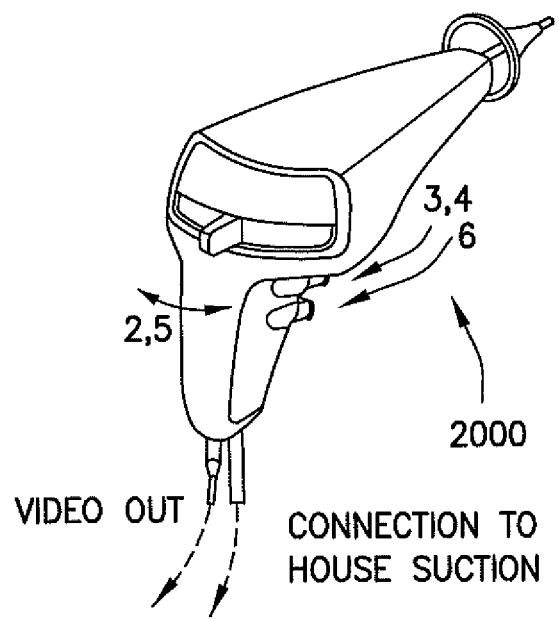
Figure 20D:
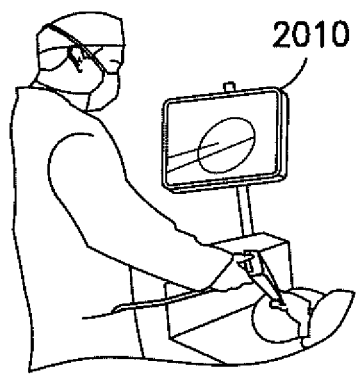

As shown in FIG. 20B, the device 2000 may be connected to house suction and Steps 3 and 4 (incision, retraction, and suction) carried out by operating a first button on a rearward facing surface of the device 2000. Step 6 (release of the ear tube 700) may be carried out by operating a second button on the rearward facing surface of the device. As shown in FIG. 20C, the display 2010 may be flipped up and swivelled, and the movement of the cutting tool 120 and suction (Steps 2 and 5) may be controlled by a slider. As shown in FIG. 20D, upon insertion of the device 2000 into a patient's ear, a surgeon may view the inside of the patient's ear on the display 2010. As shown in FIG. 20E, instead of the first and second buttons on the rearward facing surface of the device 2000 being used to carry out Steps 3, 4, and 6, buttons for controlling such functions may be located on a grip, handle, or forward facing surface of the device 2000.

Figure 21:
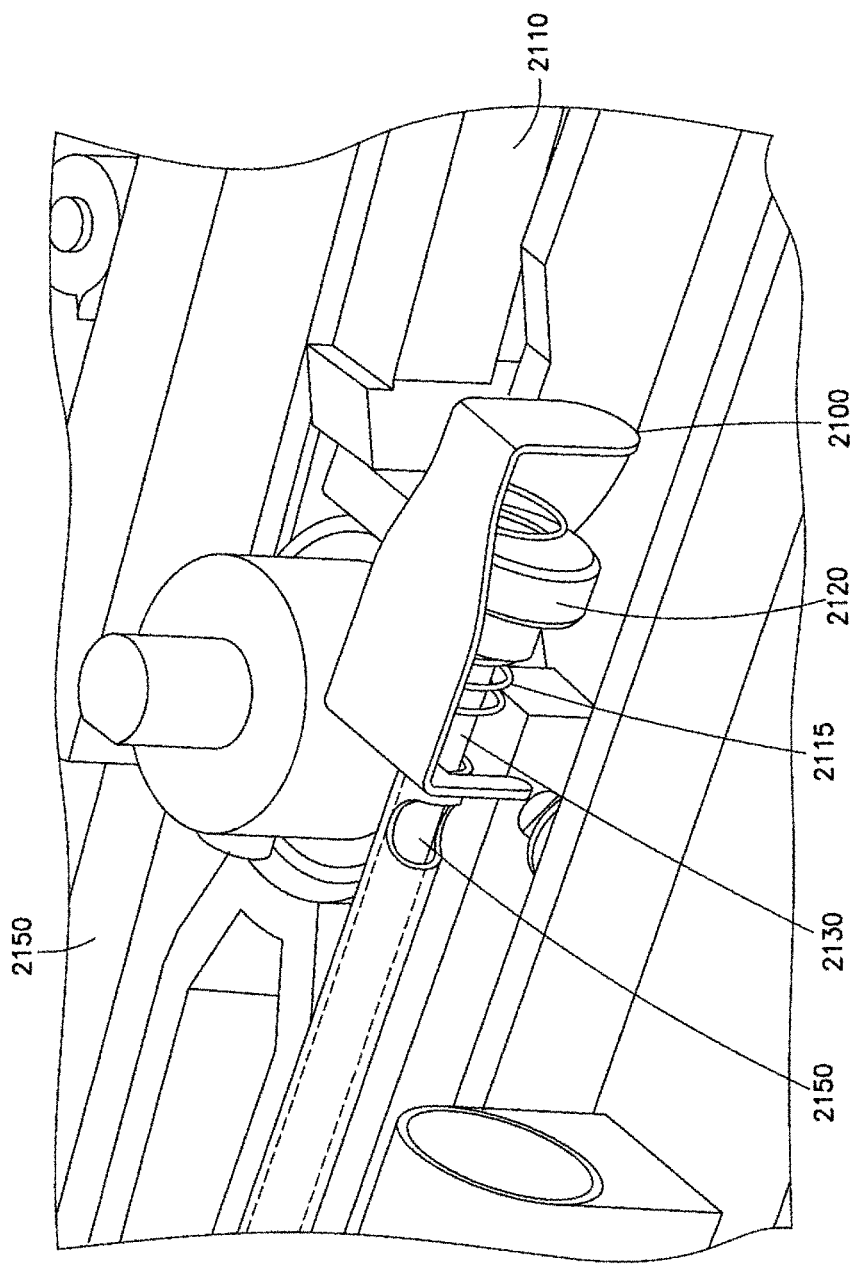
FIG. 21 is a perspective view of one example embodiment of a myringotomy device having a locking pawl that prevents proximal movement of a blade rod.

In any of the foregoing embodiments of cutting tools 120 and delivery tools 130, the blade of the cutting tool 120 may be locked in a distal position against a proximally biased force generated by a potential energy field. The surgeon may control a selectively releasable stop mechanism to retract the blade into a tube. The potential energy that proximally biases the blade rod may be a compressed spring, or a magnetic field. In embodiments using a magnetic field, the magnetic field may be repulsive field that pushes the rod proximally or an attracting field that pulls the rod proximally. There may be a finger button with a pawl-type stop that prevents the proximal movement of the blade rod. When the user presses a button, the pawl is moved and the blade rod is free to move under the influence of the potential energy source. For example, as shown in FIG. 21, a locking pawl is shown at 2100. by pushing the selectively releasable stop mechanism (shown as the slider button 2110), a cap 2120 moves forward, along with an associated blade rod 2130 that may be coupled to the knife (not shown). In doing so, a weep hole 2150 may be opened to bleed air, thus breaking suction and allowing the compressed spring 2115 to move the locking pawl 2100 and allow for the free movement (e.g., retraction) of the blade rod 2130.

The mechanism that advances the ear tube 700 (the pusher tube or sheath), whether by advancing the ear tube 700 with the sheath or advancing a carrier tube carrying the ear tube 700, may be a slider driven by the surgeon's thumb or finger. There may be a feature to provide tactile feedback as the ear tube 700 reaches its distal position. The feedback may be provided by a noiseless mechanism such as a compression spring, a compliant pad, or a repulsive magnet.

Also in any of the foregoing embodiments, to preserve line of sight the elongated shaft (and/or any portion of the device 100) may be curved or bent so that the surgeon can sight down the distal end of the device 100 without having to look past the handle. In such an embodiment, the shaft of the cutting tool 120 and/or the delivery tube 130 may be flexible in order to navigate along the curved portion of any carrier tube used to deploy the cutting tool 120 and/or the delivery tube 130.

Also in any of the foregoing embodiments, shuttling the ear tube 700 down the length of the tube to the distal end may be by the use of any suitable form of potential energy. For example, the mechanism that advances the ear tube 700 may employ springs or magnets, and a catch that prevents the distal movement of the ear tube 700 until the mechanism is tripped by a finger trigger or button. Likewise, the sheath or other device used to deploy the ear tube 700 may be biased distally by a potential energy field, but prevented from moving by a pawl-type latch. Pressing a button may release the pawl and allow the sheath to move (distally) under the influence of the potential energy field. The potential energy may be provided by a spring or a magnetic field. The magnetic field may be either repulsive or attractive.

Additionally, the devices disclosed herein may have both a blade retraction motion and a sheath advancing motion that occurs from a single user action. In one embodiment, a device may have the blade of the cutting tool 120 biased for proximal movement and the sheath biased for distal movement, but both blocked from movement by individual pawls. The surgeon may press a button which releases one of the pawls, possibly the cutting tool retraction pawl, and then continued movement of the button releases the sheath pawl. Alternatively, the button may release the sheath pawl first. In another embodiment, the first pawl is released by movement of the actuation button allowing the movement of the first element (one of the cutting tool 120 and the sheath). As the first element moves, it trips the second pawl to allow for movement of the second element (the other of the sheath and the cutting tool 120). In one embodiment, the cutting tool 120 may be biased by potential energy created by the suction line.

However, there may be mechanisms and features for breaking or stopping the moving cutting tool 120 once it has started retracting. One type of breaking mechanism may be for the end of the blade on the cutting tool 120 to be attracted to a magnet and then to come into contact with the magnet and stick to it. The mechanical shock of the collision can be reduced with a pad of foam or other compliant material. One type of breaking mechanism may be for the cutting tool 120 to be directed towards a magnetic field that repels it. The kinetic energy of the cutting tool 120 may drive against a repulsive magnetic field such that the speed at which the cutting tool 120 is retracting is reduced or stopped. In another breaking mechanism, the cutting tool 120 may travel through a ring. The end of the cutting tool 120 may have one magnet, and the ring may have one or more magnets. The fields are configured such that the end of the cutting tool 120 is attracted to the center of the ring and once there it is held in that position. This type of mechanism may act as both the accelerating and the breaking system.

If the cutting tool 120 is being drawn proximally up a suction line, it may be beneficial to stop the cutting tool 120 within the handle and before it enters the suction line, without interfering with continuous application of suction. One mechanism for stopping or breaking a moving cutting tool 120 is to drive the cutting tool 120 into a widened section of the tube within which it is traveling. Once inside the wider section, the cutting tool 120 is directed to one side of the tube, possibly by gravity or magnets, so that the cutting tool 120 does not pass into the downstream suction conduit. A device may have magnets on the side of a chamber to hold the blade of the cutting tool 120 so that it does not rattle once it is in the chamber. Alternately, the downstream suction conduit may be on a lateral side of the chamber, rather than at the axial end of the chamber, or the chamber may be curved so that a straight section of the blade of the cutting tool 120 is not able to navigate to enter into the suction line.

Furthermore, devices described herein may have a handle and an elongated blade of a cutting tool 120 with a linear blade at the distal end. The handle may have a rotating knob that rotates the proximal end of the blade shaft to reorient the blade relative to the handle. In this way the orientation of the incision can be changed without the surgeon having to twist or rotate the handle. The knob may have a tab that rides in a slot in the proximal end of the blade shaft of the cutting tool.

In one example, a myringotomy device comprises a housing; an elongated tube extending from the housing; and a retractable cutting tool extendable through the elongated tube, the cutting tool comprising a blade. The cutting tool is configured such that when advanced, the blade of the cutting tool extends beyond a distal end of the elongated tube. The cutting tool is also configured such that when retracted, the blade is retracted into the elongated tube and a fluid conduit is created from the distal end of the elongated tube to the housing.

The myringotomy device may further comprise a pinion in the housing and a carrier rack on the retractable cutting tool, the pinion and the carrier rack being configured to cooperably cause the extension and retraction of the cutting tool. The myringotomy device may further comprise a suction hose attached to the housing, the suction hose being configured to provide suction when the fluid conduit is created. The myringotomy device may further comprise a cutting tool extension button on the housing, the cutting tool extension button being configured to selectively extend or retract the cutting tool relative to the elongated tube. When the cutting tool is retracted, a weep hole in the elongated tube may be configured to be covered to cause the fluid conduit to be created. The myringotomy device may further comprise an ear tube delivery tool extendable through the elongated tube. The elongated tube may be flexible to allow the housing to be positioned out of a line of sight of a user.

In another example, a myringotomy device comprises a housing; an elongated shaft extending from the housing; an ear tube held on the outside of the elongated shaft at a chamber position that is a distance from a distal end of the elongated tube; and a movable tube configured to push or carry the ear tube over the elongated shaft to the distal end of the elongated shaft.

The movable tube configured to push or carry the ear tube may be actuatable via a trigger on the housing. The myringotomy device may further comprise a spring coupled to the trigger, the spring being configured to indicate an amount of force back to a user as feedback to determine a distance from the ear tube to the distal end of the elongated tube. The elongated shaft may comprise a hollow tube operable as a fluid conduit. The elongated shaft may comprise a solid rod.

In another example, a myringotomy tool may comprise a housing and an extended shaft having a distal end with at least one tool located at the distal end. The extended shaft has a bend between the proximal end and the distal end of the shaft such that the straight length of shaft distal to the bend can be viewed on axis.

The at least one tool may comprise one or more of a cutting tool, an ear tube delivery tool, a suction tool, an irrigation tool, and a viewing tool. The extended shaft may be hollow and the at least one tool may be retractable into the extended shaft. The extended shaft may be solid and an ear tube delivery tool may be extendable over the solid extended shaft.

In another example, a myringotomy tool comprises a handpiece; an elongated tube extending from the handpiece; a blade shaft extending down the elongated tube and being extendable beyond a distal end of the elongated tube; and a knob on the handpiece, the knob being cooperably coupled to the blade shaft. The knob is configured to rotate the blade shaft when turned. The blade shaft may be retractable into the elongated tube.

In another example, a myringotomy device may comprise a housing; a speculum coupled to the housing; two or more tools located in the housing, each of the two or more tools being coupled to a distal end of a tool carrier in the housing; and a linkage for delivering each of the two or more tools serially through the speculum.

The two or more tools may comprise at least a cutting tool and an ear tube delivery tool. The two or more tools may further comprise at least one of a suction tool and an imaging tool. The linkage may be coupled to a sliding actuator.

In another example, a method of performing a myringotomy procedure comprises causing a retractable cutting tool to extend through a hollow elongated tube depending from a housing, the cutting tool comprising a blade; making an incision in an ear drum using the retractable cutting tool; retracting the retractable cutting tool; and causing an ear tube to be delivered from the elongated tube to the incision.

The method may further comprise causing suction to be formed in the elongated tube and suctioning the ear drum before delivery of the ear tube. Causing an ear tube to be delivered from the elongated tube to the incision may comprise one of pushing the ear tube from a distal end of the elongated tube and into the incision and carrying the ear tube over the elongated tube to the incision and pushing the ear tube into the incision.

In another example, a method of assembling a myringotomy tool comprises providing a housing; extending an elongated shaft from the housing; providing at least a cutting tool and an ear tube delivery tool in the housing; and causing the cutting tool and the ear tube delivery tool to be serially deliverable from a distal end of the elongated shaft.

Causing the cutting tool and the ear tube delivery tool to be serially deliverable may comprise causing the cutting tool and the ear tube delivery tool to be movable using a pinion and a carrier rack. Causing the cutting tool and the ear tube delivery tool to be serially deliverable may comprise causing the cutting tool and the ear tube delivery tool to be movable using slider mechanisms.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

We claim:

1. A method of performing a myringotomy procedure, the method comprising:
   causing a retractable cutting tool to extend through a hollow elongated tube from a retracted position to an extended position relative to the hollow elongated tube, the hollow elongated tube extending from a housing, and the retractable cutting tool comprising a blade, wherein causing the retractable cutting tool to extend through the hollow elongated tube to the extended position seals the hollow elongated tube;
   making an incision in an ear drum using the retractable cutting tool;
   retracting the retractable cutting tool; and
   causing an ear tube to be delivered from the hollow elongated tube to the incision.

2. The method of claim 1, further comprising causing suction to be formed in the hollow elongated tube and suctioning the ear drum before delivery of the ear tube.

3. The method of claim 1, wherein causing the ear tube to be delivered from the hollow elongated tube to the incision comprises pushing the ear tube from a distal end of the hollow elongated tube and into the incision.

4. The method of claim 1, wherein causing the ear tube to be delivered from the hollow elongated tube to the incision comprises carrying the ear tube over the hollow elongated tube to the incision and pushing the ear tube into the incision.

5. The method of claim 1, wherein causing the retractable cutting tool to extend through the hollow elongated tube comprises causing the retractable cutting tool to extend beyond a distal end of the hollow elongated tube.

6. The method of claim 1, wherein retracting the retractable cutting tool to the retracted position creates a fluid conduit through the hollow elongated tube.

7. The method of claim 1, further comprising a knob on the housing, the knob being operably coupled to the hollow elongated tube.

8. The method of claim 7, wherein the knob is configured to rotate the hollow elongated tube when turned.

9. A method of performing a myringotomy procedure, the method comprising:
   causing a retractable cutting tool to extend through a hollow elongated tube to an extended position relative to the hollow elongated tube, wherein the retractable cutting tool seals the hollow elongated tube in the extended position;
   making an incision in an ear drum using the retractable cutting tool;
   retracting the retractable cutting tool to a retracted position relative to the hollow elongated tube; and
   causing an ear tube to be delivered from the hollow elongated tube to the incision.

10. The method of claim 9, wherein the retractable cutting tool comprises a blade.

11. The method of claim 9, wherein causing the ear tube to be delivered from the hollow elongated tube to the incision comprises pushing or carrying the ear tube with a movable tube mounted on the hollow elongated tube.

12. The method of claim 11, wherein the ear tube is held on an outer surface of the hollow elongated tube prior to being delivered to the incision.

13. The method of claim 12, wherein the movable tube is actuatable via a trigger.

14. The method of claim 9, wherein the hollow elongated tube comprises one or more of a suction tool, an irrigation tool, and a viewing tool.

15. The method of claim 9, further comprising causing suction to be formed in the hollow elongated tube and suctioning the ear drum before delivery of the ear tube.

16. A method of performing a myringotomy procedure, the method comprising:
   causing a cutting tool to move from a retracted position within a hollow elongated tube to an extended position at least partially outside of the hollow elongated tube;
   making an incision in an ear drum using the cutting tool in the extended position;
   causing the cutting tool to move from the extended position to the retracted position; and
   causing an ear tube to be delivered from the hollow elongated tube to the incision;

wherein the cutting tool seals the hollow elongated tube in the extended position and creates a fluid conduit through the hollow elongated tube in the retracted position.

17. The method of claim 16, wherein the cutting tool comprises a blade.

18. The method of claim 16, further comprising causing suction to be formed in the hollow elongated tube and suctioning the ear drum before delivery of the ear tube.

* * * * *